US011596429B2

United States Patent
Gannon et al.

(10) Patent No.: US 11,596,429 B2
(45) Date of Patent: Mar. 7, 2023

(54) TISSUE RESECTING INSTRUMENT

(71) Applicant: Covidien LP, Mansfield, MA (US)

(72) Inventors: Alan P. Gannon, Amesbury, MA (US); Dalia P. Leibowitz, Cambridge, MA (US); Peter F. Marshall, Bolton, MA (US)

(73) Assignee: Covidien LP, Mansfield, MA (US)

( * ) Notice: Subject to any disclaimer, the term of this patent is extended or adjusted under 35 U.S.C. 154(b) by 414 days.

(21) Appl. No.: 16/852,752

(22) Filed: Apr. 20, 2020

(65) Prior Publication Data

US 2021/0322048 A1    Oct. 21, 2021

(51) Int. Cl.
| | | |
|---|---|---|
| A61B 17/32 | (2006.01) | |
| A61B 34/37 | (2016.01) | |
| A61B 17/00 | (2006.01) | |
| A61B 17/42 | (2006.01) | |

(52) U.S. Cl.
CPC ........ *A61B 17/32002* (2013.01); *A61B 34/37* (2016.02); *A61B 2017/0023* (2013.01); *A61B 2017/00477* (2013.01); *A61B 2017/00734* (2013.01); *A61B 2017/320032* (2013.01); *A61B 2017/4216* (2013.01); *A61B 2217/005* (2013.01)

(58) Field of Classification Search
CPC .. A61B 17/32002; A61B 2017/320032; A61B 34/37; A61B 2017/0023; A61B 2017/00477; A61B 2017/00734; A61B 2017/4216; A61B 2217/005
See application file for complete search history.

(56) References Cited

U.S. PATENT DOCUMENTS

| | | | |
|---|---|---|---|
| 1,585,934 A | 5/1926 | Muir | |
| 1,666,332 A | 4/1928 | Hirsch | |
| 1,831,786 A | 11/1931 | Duncan | |
| 2,708,437 A | 5/1955 | Hutchins | |

(Continued)

FOREIGN PATENT DOCUMENTS

| | | | |
|---|---|---|---|
| DE | 3339322 A1 | 5/1984 | |
| DE | 3206381 C2 | 7/1986 | |

(Continued)

OTHER PUBLICATIONS

Extended European Search Report issued in corresponding European Application No. 21169301.5 dated Sep. 22, 2021, 8 pages.

*Primary Examiner* — Ashley L Fishback
(74) *Attorney, Agent, or Firm* — Carter, DeLuca & Farrell LLP

(57) ABSTRACT

An end effector assembly of a tissue-resecting device includes an outer shaft defining a window, a drive wire extending through the outer shaft, and a distal cutting tip disposed within the outer shaft. The drive wire includes a cylindrical body and a distal end portion defining a semi-cylindrical configuration including a semi-cylindrical bottom surface and a planar top surface having a semi-cylindrical cut-out defined therein. The distal cutting tip at least partially overlaps the window and has a semi-cylindrical lumen defined by a semi-cylindrical bottom surface and an open top. The distal end portion of the drive wire is at least partially received and within the semi-cylindrical lumen with the semi-cylindrical surfaces substantially mating. The drive wire is configured to drive rotation or oscillation of the distal cutting tip relative to the outer shaft.

17 Claims, 17 Drawing Sheets

(56) References Cited

U.S. PATENT DOCUMENTS

| | | |
|---|---|---|
| 3,297,022 A | 1/1967 | Wallace |
| 3,686,706 A | 8/1972 | Finley |
| 3,734,099 A | 5/1973 | Bender et al. |
| 3,791,379 A | 2/1974 | Storz |
| 3,812,855 A | 5/1974 | Banko |
| 3,835,842 A | 9/1974 | Iglesias |
| 3,850,162 A | 11/1974 | Iglesias |
| 3,945,375 A | 3/1976 | Banko |
| 3,980,252 A | 9/1976 | Tae |
| 3,995,619 A | 12/1976 | Glatzer |
| 3,996,921 A | 12/1976 | Neuwirth |
| 4,011,869 A | 3/1977 | Seiler, Jr. |
| 4,108,182 A | 8/1978 | Hartman et al. |
| 4,146,405 A | 3/1979 | Timmer et al. |
| 4,198,958 A | 4/1980 | Utsugi |
| 4,203,444 A | 5/1980 | Bonnell et al. |
| 4,210,146 A | 7/1980 | Banko |
| 4,246,902 A | 1/1981 | Martinez |
| 4,247,180 A | 1/1981 | Norris |
| 4,258,721 A | 3/1981 | Parent et al. |
| 4,261,346 A | 4/1981 | Wettermann |
| 4,294,234 A | 10/1981 | Matsuo |
| 4,316,465 A | 2/1982 | Dotson, Jr. |
| 4,369,768 A | 1/1983 | Vukovic |
| 4,392,485 A | 7/1983 | Hiltebrandt |
| 4,414,962 A | 11/1983 | Carson |
| 4,449,538 A | 5/1984 | Corbitt et al. |
| 4,493,698 A | 1/1985 | Wang et al. |
| 4,517,977 A | 5/1985 | Frost |
| 4,543,965 A | 10/1985 | Pack et al. |
| 4,567,880 A | 2/1986 | Goodman |
| 4,589,414 A | 5/1986 | Yoshida et al. |
| 4,601,284 A | 7/1986 | Arakawa et al. |
| 4,601,290 A | 7/1986 | Effron et al. |
| 4,606,330 A | 8/1986 | Bonnet |
| 4,630,598 A | 12/1986 | Bonnet |
| 4,644,952 A | 2/1987 | Patipa et al. |
| 4,649,919 A | 3/1987 | Fhimsen et al. |
| 4,700,694 A | 10/1987 | Shishido |
| 4,706,656 A | 11/1987 | Kuboto |
| 4,718,291 A | 1/1988 | Wood et al. |
| 4,737,142 A | 4/1988 | Heckele |
| 4,749,376 A | 6/1988 | Kensey et al. |
| 4,756,309 A | 7/1988 | Sachse et al. |
| 4,819,635 A | 4/1989 | Shapiro |
| 4,844,064 A | 7/1989 | Thimsen et al. |
| 4,850,354 A | 7/1989 | McGurk-Burleson et al. |
| 4,856,919 A | 8/1989 | Takeuchi et al. |
| 4,867,157 A | 9/1989 | McGurk-Burleson et al. |
| 4,924,851 A | 5/1990 | Ognier et al. |
| 4,940,061 A | 7/1990 | Terwilliger et al. |
| 4,950,278 A | 8/1990 | Sachse et al. |
| 4,955,882 A | 9/1990 | Hakky |
| 4,971,034 A | 11/1990 | Doi et al. |
| 4,986,827 A | 1/1991 | Akkas et al. |
| 4,998,527 A | 3/1991 | Meyer |
| 4,998,914 A | 3/1991 | Wiest et al. |
| 5,007,917 A | 4/1991 | Evans |
| 5,027,792 A | 7/1991 | Meyer |
| 5,037,386 A | 8/1991 | Marcus et al. |
| 5,105,800 A | 4/1992 | Takahashi et al. |
| 5,106,364 A | 4/1992 | Hayafuji et al. |
| 5,112,299 A | 5/1992 | Pascaloff |
| 5,116,868 A | 5/1992 | Chen et al. |
| 5,125,910 A | 6/1992 | Freitas |
| 5,133,713 A | 7/1992 | Huang et al. |
| 5,152,744 A | 10/1992 | Krause et al. |
| 5,158,553 A | 10/1992 | Berry et al. |
| 5,163,433 A | 11/1992 | Kagawa et al. |
| 5,169,397 A | 12/1992 | Sakashita et al. |
| 5,176,677 A | 1/1993 | Wuchinich |
| 5,195,541 A | 3/1993 | Obenchain |
| 5,226,910 A | 7/1993 | Kajiyama et al. |
| 5,244,459 A | 9/1993 | Hill |
| 5,254,117 A | 10/1993 | Rigby et al. |
| 5,269,785 A | 12/1993 | Bonutti |
| 5,270,622 A | 12/1993 | Krause |
| 5,275,609 A | 1/1994 | Pingleton et al. |
| 5,288,290 A | 2/1994 | Brody |
| 5,304,118 A | 4/1994 | Trese et al. |
| 5,312,399 A | 5/1994 | Hakky et al. |
| 5,312,425 A | 5/1994 | Evans et al. |
| 5,312,430 A | 5/1994 | Rosenbluth et al. |
| 5,320,091 A | 6/1994 | Grossi et al. |
| 5,347,992 A | 9/1994 | Pearlman et al. |
| 5,350,390 A | 9/1994 | Sher |
| 5,364,395 A | 11/1994 | West, Jr. |
| 5,374,253 A | 12/1994 | Burns, Sr. et al. |
| 5,390,585 A | 2/1995 | Ryuh |
| 5,392,765 A | 2/1995 | Muller |
| 5,395,313 A | 3/1995 | Naves et al. |
| 5,403,276 A | 4/1995 | Schechter et al. |
| 5,409,013 A | 4/1995 | Clement |
| 5,409,453 A | 4/1995 | Lundquist et al. |
| 5,411,513 A | 5/1995 | Ireland et al. |
| 5,421,819 A | 6/1995 | Edwards et al. |
| 5,425,376 A | 6/1995 | Banys et al. |
| 5,429,601 A | 7/1995 | Conley et al. |
| 5,435,805 A | 7/1995 | Edwards et al. |
| 5,443,476 A | 8/1995 | Shapiro |
| 5,449,356 A | 9/1995 | Walbrink et al. |
| 5,456,673 A | 10/1995 | Ziegler et al. |
| 5,456,689 A | 10/1995 | Kresch et al. |
| 5,483,951 A | 1/1996 | Frassica et al. |
| 5,490,819 A | 2/1996 | Nicholas et al. |
| 5,490,860 A | 2/1996 | Middle et al. |
| 5,492,537 A | 2/1996 | Vancaillie |
| 5,498,258 A | 3/1996 | Hakky et al. |
| 5,527,331 A | 6/1996 | Kresch et al. |
| 5,549,541 A | 8/1996 | Muller |
| 5,556,378 A | 9/1996 | Storz et al. |
| 5,563,481 A | 10/1996 | Krause |
| 5,569,164 A | 10/1996 | Lurz |
| 5,569,254 A | 10/1996 | Carlson et al. |
| 5,569,284 A | 10/1996 | Young et al. |
| 5,575,756 A | 11/1996 | Karasawa et al. |
| 5,586,973 A | 12/1996 | Lemaire et al. |
| 5,591,187 A | 1/1997 | Dekel |
| 5,601,583 A | 2/1997 | Donahue et al. |
| 5,601,603 A | 2/1997 | Illi |
| 5,602,449 A | 2/1997 | Krause et al. |
| 5,603,332 A | 2/1997 | O'Connor |
| 5,630,798 A | 5/1997 | Beiser et al. |
| 5,649,547 A | 7/1997 | Ritchart et al. |
| 5,669,927 A | 9/1997 | Boebel et al. |
| 5,672,945 A | 9/1997 | Krause |
| 5,674,179 A | 10/1997 | Bonnet et al. |
| 5,676,497 A | 10/1997 | Kim |
| 5,695,448 A | 12/1997 | Kimura et al. |
| 5,702,420 A | 12/1997 | Sterling et al. |
| 5,709,698 A | 1/1998 | Adams et al. |
| 5,730,752 A | 3/1998 | Alden et al. |
| 5,733,298 A | 3/1998 | Berman et al. |
| 5,741,286 A | 4/1998 | Recuset |
| 5,741,287 A | 4/1998 | Alden et al. |
| 5,749,885 A | 5/1998 | Sjostrom et al. |
| 5,749,889 A | 5/1998 | Bacich et al. |
| 5,759,185 A | 6/1998 | Grinberg |
| 5,772,634 A | 6/1998 | Atkinson |
| 5,775,333 A | 7/1998 | Burbank et al. |
| 5,782,849 A | 7/1998 | Miller |
| 5,807,240 A | 9/1998 | Muller et al. |
| 5,807,282 A | 9/1998 | Fowler |
| 5,810,770 A | 9/1998 | Chin et al. |
| 5,810,861 A | 9/1998 | Gaber |
| 5,814,009 A | 9/1998 | Wheatman |
| 5,833,643 A | 11/1998 | Ross et al. |
| 5,840,060 A | 11/1998 | Beiser et al. |
| 5,857,995 A | 1/1999 | Thomas et al. |
| 5,873,886 A | 2/1999 | Larsen et al. |
| 5,899,915 A | 5/1999 | Saadat |
| 5,911,699 A | 6/1999 | Anis et al. |
| 5,911,722 A | 6/1999 | Adler et al. |
| 5,913,867 A | 6/1999 | Dion |

(56) References Cited

U.S. PATENT DOCUMENTS

| | | |
|---|---|---|
| 5,916,229 A | 6/1999 | Evans |
| 5,925,055 A | 7/1999 | Adrian et al. |
| 5,928,163 A | 7/1999 | Roberts et al. |
| 5,944,668 A | 8/1999 | Vancaillie et al. |
| 5,947,990 A | 9/1999 | Smith |
| 5,951,490 A | 9/1999 | Fowler |
| 5,956,130 A | 9/1999 | Vancaillie et al. |
| 5,957,832 A | 9/1999 | Taylor et al. |
| 6,001,116 A | 12/1999 | Heisler et al. |
| 6,004,320 A | 12/1999 | Casscells et al. |
| 6,007,513 A | 12/1999 | Anis et al. |
| 6,024,751 A | 2/2000 | Lovato et al. |
| 6,032,673 A | 3/2000 | Savage et al. |
| 6,039,748 A | 3/2000 | Savage et al. |
| 6,042,552 A | 3/2000 | Cornier |
| 6,068,641 A | 5/2000 | Varsseveld |
| 6,086,542 A | 7/2000 | Glowa et al. |
| 6,090,094 A | 7/2000 | Clifford, Jr. et al. |
| 6,090,123 A | 7/2000 | Culp et al. |
| 6,113,594 A | 9/2000 | Savage |
| 6,119,973 A | 9/2000 | Galloway |
| 6,120,147 A | 9/2000 | Vijfvinkel et al. |
| 6,120,462 A | 9/2000 | Hibner et al. |
| 6,132,448 A | 10/2000 | Perez et al. |
| 6,149,633 A | 11/2000 | Maaskamp |
| 6,156,049 A | 12/2000 | Lovato et al. |
| 6,159,160 A | 12/2000 | Hsei et al. |
| 6,159,209 A | 12/2000 | Hakky |
| 6,203,518 B1 | 3/2001 | Anis et al. |
| 6,217,543 B1 | 4/2001 | Anis et al. |
| 6,224,603 B1 | 5/2001 | Marino |
| 6,244,228 B1 | 6/2001 | Kuhn et al. |
| 6,251,120 B1 | 6/2001 | Dorn |
| 6,258,111 B1 | 7/2001 | Ross et al. |
| 6,277,096 B1 | 8/2001 | Cortella et al. |
| 6,315,714 B1 | 11/2001 | Akiba |
| 6,358,200 B1 | 3/2002 | Grossi |
| 6,358,263 B2 | 3/2002 | Mark et al. |
| 6,359,200 B1 | 3/2002 | Day |
| 6,402,701 B1 | 6/2002 | Kaplan et al. |
| 6,428,486 B2 | 8/2002 | Ritchart et al. |
| 6,471,639 B2 | 10/2002 | Rudischhauser et al. |
| 6,494,892 B1 | 12/2002 | Ireland et al. |
| 6,585,708 B1 | 7/2003 | Maaskamp |
| 6,610,066 B2 | 8/2003 | Dinger et al. |
| 6,626,827 B1 | 9/2003 | Felix et al. |
| 6,632,182 B1 | 10/2003 | Treat |
| 6,656,132 B1 | 12/2003 | Ouchi |
| 6,712,773 B1 | 3/2004 | Viola |
| 6,824,544 B2 | 11/2004 | Boebel et al. |
| 6,837,847 B2 | 1/2005 | Ewers et al. |
| 7,025,720 B2 | 4/2006 | Boebel et al. |
| 7,025,732 B2 | 4/2006 | Thompson et al. |
| 7,150,713 B2 | 12/2006 | Shener et al. |
| 7,226,459 B2 | 6/2007 | Cesarini et al. |
| 7,249,602 B1 | 7/2007 | Emanuel |
| 7,510,563 B2 | 3/2009 | Cesarini et al. |
| 7,763,033 B2 | 7/2010 | Gruber et al. |
| 7,922,737 B1 | 4/2011 | Cesarini et al. |
| 8,025,656 B2 | 9/2011 | Gruber et al. |
| 8,061,359 B2 | 11/2011 | Emanuel |
| 8,062,214 B2 | 11/2011 | Shener et al. |
| 8,157,826 B2 | 4/2012 | Deng et al. |
| 8,419,626 B2 | 4/2013 | Shener-Irmakoglu et al. |
| 8,444,592 B2 | 5/2013 | Williams et al. |
| 8,465,421 B2 | 6/2013 | Finkman et al. |
| 8,500,769 B2 | 8/2013 | Deng |
| 8,528,563 B2 | 9/2013 | Gruber |
| 8,568,424 B2 | 10/2013 | Shugrue et al. |
| 8,574,253 B2 | 11/2013 | Gruber et al. |
| 8,597,228 B2 | 12/2013 | Pyles et al. |
| 8,647,349 B2 | 2/2014 | Gruber et al. |
| 8,663,264 B2 | 3/2014 | Cesarini et al. |
| 8,678,999 B2 | 3/2014 | Isaacson |
| 8,834,487 B2 | 9/2014 | Gruber et al. |
| 8,840,625 B2 | 9/2014 | Adams et al. |
| 8,840,626 B2 | 9/2014 | Adams et al. |
| 8,852,085 B2 | 10/2014 | Shener-Irmakoglu et al. |
| 8,893,722 B2 | 11/2014 | Emanuel |
| 8,932,208 B2 | 1/2015 | Kendale et al. |
| 8,951,274 B2 | 2/2015 | Adams et al. |
| 9,060,760 B2 | 6/2015 | Sullivan et al. |
| 9,060,800 B1 | 6/2015 | Cesarini et al. |
| 9,060,801 B1 | 6/2015 | Cesarini et al. |
| 9,066,745 B2 | 6/2015 | Cesarini et al. |
| 9,072,431 B2 | 7/2015 | Adams et al. |
| 9,089,358 B2 | 7/2015 | Emanuel |
| 9,095,366 B2 | 8/2015 | Sullivan et al. |
| 9,125,550 B2 | 9/2015 | Shener-Lrmakoglu et al. |
| 9,155,454 B2 | 10/2015 | Sahney et al. |
| 9,259,233 B2 | 2/2016 | Gruber et al. |
| 9,474,848 B2 | 10/2016 | Williams et al. |
| 10,376,278 B2 | 8/2019 | Fojtik et al. |
| 2008/0058842 A1 | 3/2008 | Emanuel |
| 2008/0097468 A1 | 4/2008 | Adams et al. |
| 2008/0097469 A1 | 4/2008 | Gruber et al. |
| 2008/0097470 A1 | 4/2008 | Gruber et al. |
| 2008/0097471 A1 | 4/2008 | Adams et al. |
| 2008/0135053 A1 | 6/2008 | Gruber et al. |
| 2008/0146872 A1 | 6/2008 | Gruber et al. |
| 2008/0146873 A1 | 6/2008 | Adams et al. |
| 2008/0245371 A1 | 10/2008 | Gruber |
| 2008/0249366 A1 | 10/2008 | Gruber et al. |
| 2008/0249534 A1 | 10/2008 | Gruber et al. |
| 2008/0249553 A1 | 10/2008 | Gruber et al. |
| 2008/0262308 A1 | 10/2008 | Prestezog et al. |
| 2009/0082628 A1 | 3/2009 | Kucklick et al. |
| 2009/0270812 A1 | 10/2009 | Litscher et al. |
| 2009/0270895 A1 | 10/2009 | Churchill et al. |
| 2009/0270896 A1 | 10/2009 | Sullivan et al. |
| 2009/0270897 A1 | 10/2009 | Adams et al. |
| 2009/0270898 A1 | 10/2009 | Chin et al. |
| 2010/0087798 A1 | 4/2010 | Adams et al. |
| 2010/0152647 A1 | 6/2010 | Shener et al. |
| 2011/0034943 A1 | 2/2011 | Churchill et al. |
| 2011/0077674 A1 | 3/2011 | Sullivan et al. |
| 2011/0118544 A1 | 5/2011 | Adams et al. |
| 2011/0166419 A1 | 7/2011 | Reif et al. |
| 2012/0067352 A1 | 3/2012 | Gruber et al. |
| 2012/0078038 A1 | 3/2012 | Sahney et al. |
| 2013/0131452 A1 | 5/2013 | Kuroda et al. |
| 2014/0003183 A1 | 1/2014 | Song |
| 2015/0305765 A1 | 10/2015 | Fojtik et al. |
| 2017/0189046 A1 | 7/2017 | Fojtik et al. |

FOREIGN PATENT DOCUMENTS

| | | |
|---|---|---|
| DE | 3601453 A1 | 9/1986 |
| DE | 3615694 A1 | 11/1987 |
| DE | 4038398 A1 | 6/1992 |
| DE | 4440035 A1 | 5/1996 |
| DE | 19633124 A1 | 5/1997 |
| DE | 19751632 C1 | 9/1999 |
| DE | 102006022827 A1 | 12/2006 |
| EP | 0310285 A2 | 4/1989 |
| EP | 0327410 A1 | 8/1989 |
| EP | 0557044 A1 | 8/1993 |
| EP | 0582295 A2 | 2/1994 |
| EP | 0606531 A2 | 7/1994 |
| EP | 0621008 A2 | 10/1994 |
| EP | 0806183 A1 | 11/1997 |
| EP | 1681022 A1 | 7/2006 |
| EP | 3868316 A1 | 8/2021 |
| GB | 2093353 A | 9/1982 |
| GB | 2311468 A | 10/1997 |
| JP | 2001075416 A | 3/2001 |
| JP | 2002529185 A | 9/2002 |
| JP | 2002538889 A | 11/2002 |
| JP | 2003245247 A | 9/2003 |
| NL | 1006944 C2 | 3/1999 |
| WO | 8101648 A1 | 6/1981 |
| WO | 9211816 A2 | 7/1992 |
| WO | 9307821 A1 | 4/1993 |
| WO | 9315664 A1 | 8/1993 |

(56) References Cited

FOREIGN PATENT DOCUMENTS

| | | | |
|---|---|---|---|
| WO | 9426181 A1 | 11/1994 |
| WO | 9505777 A1 | 3/1995 |
| WO | 9510981 A1 | 4/1995 |
| WO | 9510982 A1 | 4/1995 |
| WO | 9522935 A1 | 8/1995 |
| WO | 9530377 A1 | 11/1995 |
| WO | 9611638 A1 | 4/1996 |
| WO | 9626676 A1 | 9/1996 |
| WO | 9709922 A1 | 3/1997 |
| WO | 9717027 A1 | 5/1997 |
| WO | 9719642 A1 | 6/1997 |
| WO | 9724071 A1 | 7/1997 |
| WO | 9734534 A1 | 9/1997 |
| WO | 9735522 A1 | 10/1997 |
| WO | 9809569 A1 | 3/1998 |
| WO | 9810707 A1 | 3/1998 |
| WO | 9846147 A1 | 10/1998 |
| WO | 9903407 A1 | 1/1999 |
| WO | 9903409 A1 | 1/1999 |
| WO | 9907295 A1 | 2/1999 |
| WO | 9911184 A1 | 3/1999 |
| WO | 9939648 A1 | 8/1999 |
| WO | 9944506 A1 | 9/1999 |
| WO | 9960935 A1 | 12/1999 |
| WO | 0012010 A1 | 3/2000 |
| WO | 0028890 A1 | 5/2000 |
| WO | WO-0025682 A1 * | 5/2000 | ....... A61B 17/32002 |
| WO | 0033743 A1 | 6/2000 |
| WO | 0044295 A1 | 8/2000 |
| WO | 0047116 A1 | 8/2000 |
| WO | 0057797 A1 | 10/2000 |
| WO | 0135831 A1 | 5/2001 |
| WO | 0158368 A1 | 8/2001 |
| WO | 0195810 A2 | 12/2001 |
| WO | 02069808 A2 | 9/2002 |
| WO | 03022164 A1 | 3/2003 |
| WO | 03077767 A1 | 9/2003 |
| WO | 2005060842 A1 | 7/2005 |
| WO | 2005096963 A2 | 10/2005 |
| WO | 2006105283 A2 | 10/2006 |
| WO | 2006121968 A2 | 11/2006 |
| WO | 2006121970 A2 | 11/2006 |
| WO | 2007044833 A2 | 4/2007 |
| WO | 2012044705 A1 | 4/2012 |

* cited by examiner

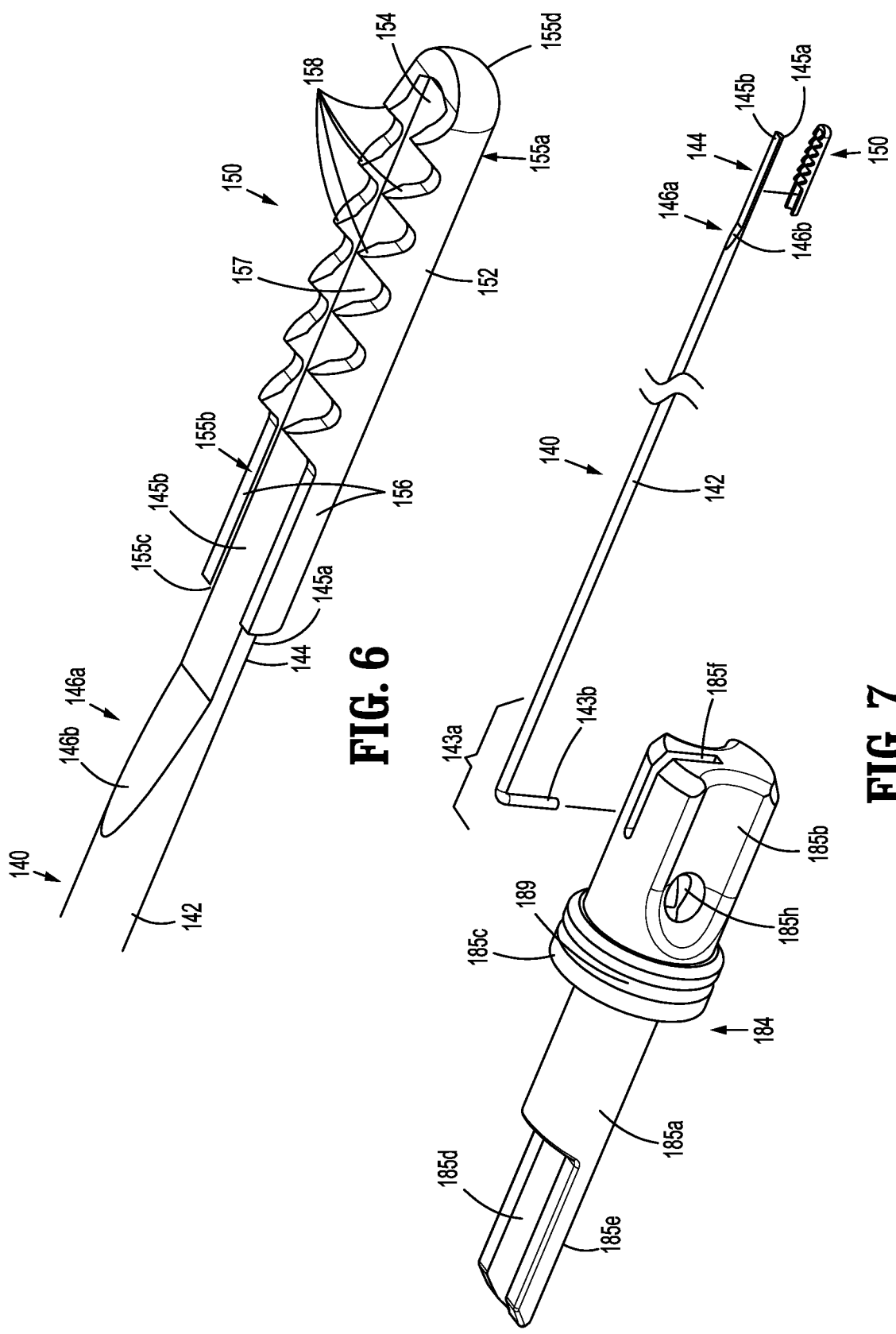

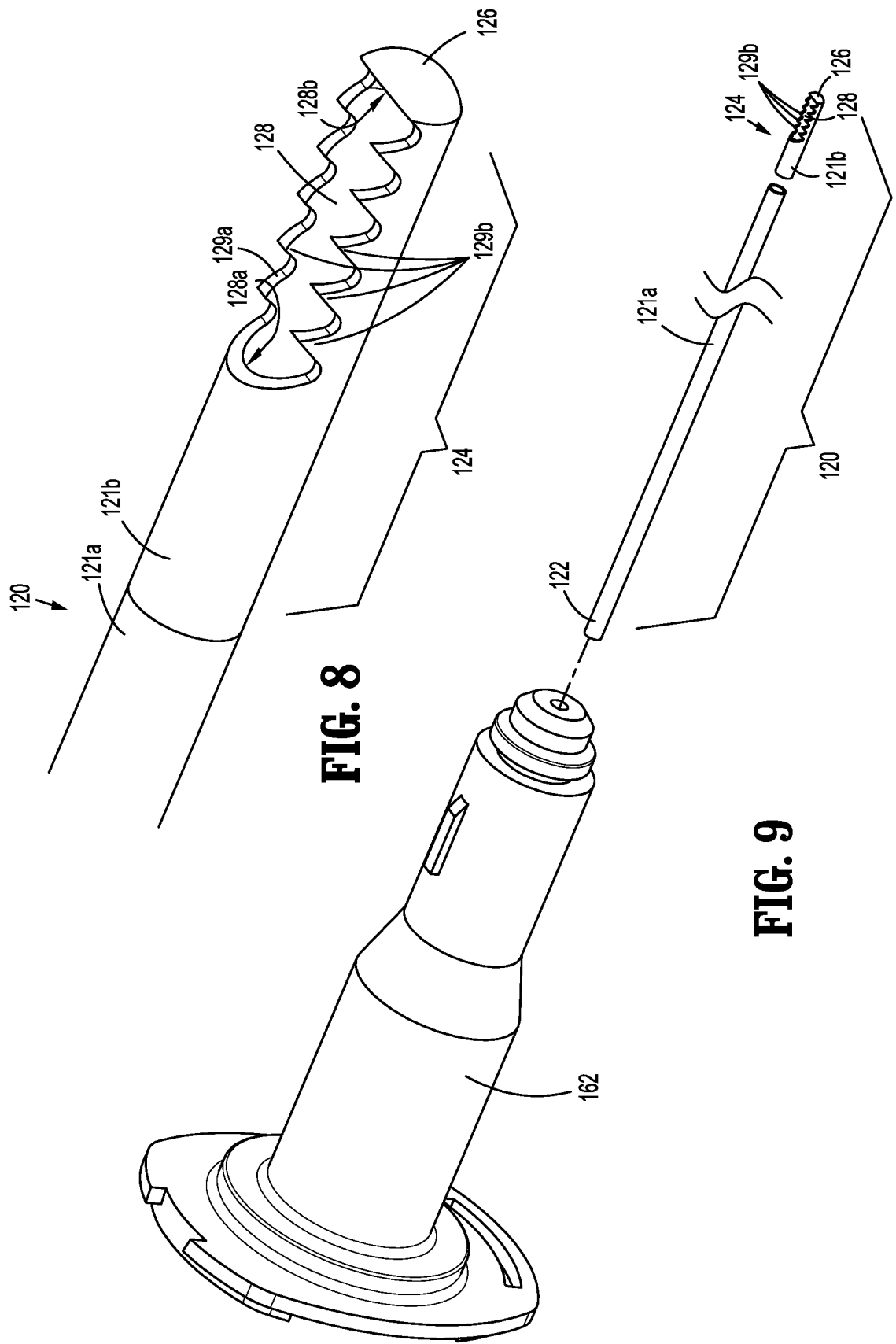

TISSUE RESECTING INSTRUMENT

BACKGROUND

1. Technical Field

The present disclosure relates generally to the field of tissue resection. In particular, the present disclosure relates to a tissue resecting instrument configured to facilitate resection and removal of tissue from an internal surgical site, e.g., a uterus.

2. Background of Related Art

Tissue resection may be performed endoscopically within an organ, such as a uterus, by inserting an endoscope (or hysteroscope) into the uterus and passing a tissue resection instrument through the endoscope (or hysteroscope) and into the uterus. With respect to such endoscopic tissue resection procedures, it often is desirable to distend the uterus with a fluid, for example, saline, sorbitol, or glycine. The inflow and outflow of the fluid during the procedure maintains the uterus in a distended state and flushes tissue and other debris from within the uterus to maintain a visible working space.

SUMMARY

As used herein, the term "distal" refers to the portion that is described which is further from a user, while the term "proximal" refers to the portion that is described which is closer to a user. Further, to the extent consistent, any or all of the aspects described herein may be used in conjunction with any or all of the other aspects described herein.

Provided in accordance with aspects of the present disclosure is an end effector assembly of a tissue-resecting device including an outer shaft, a drive wire, a distal cutting tip, a hub housing, and a driver. The outer shaft defines a proximal end portion and a distal end portion. The distal end portion of the outer shaft defines a window therethrough. The drive wire extends through the outer shaft and defines a proximal end portion and a distal end portion. The distal cutting tip is disposed within the outer shaft and engaged with the distal end portion of the drive wire. The distal cutting tip at least partially overlaps the window. The hub housing is engaged with the proximal end portion of the outer shaft. The driver is disposed within the hub housing and is engaged with the proximal end portion of the drive wire. The driver is configured to be driven to rotate relative to the hub housing to thereby rotate the drive wire and distal cutting tip within and relative to the outer shaft. The driver defines an internal lumen and at least one lateral opening disposed in communication with the internal lumen. An outflow path is defined from the window through the outer shaft and about the drive wire, into an interior of the hub housing, through the at least one lateral opening, and through the internal lumen.

In an aspect of the present disclosure, the outer shaft includes a cutting edge surrounding the window. The cutting edge defines a plurality of cutting teeth.

In another aspect of the present disclosure the distal cutting tip defines a mouth in communication with the window in at least one rotational orientation of the distal cutting tip relative to the outer shaft. In such aspects, the outflow path may further be defined from the window through the mouth, through outer shaft and about the drive wire, into an interior of the hub housing, through the at least one lateral opening, and through the internal lumen. Additionally or alternatively, the distal cutting tip may include a plurality of teeth disposed along opposing sides of the mouth.

In yet another aspect of the present disclosure, a proximal extension extends proximally from the hub housing and defines an interior in fluid communication with the internal lumen such that the outflow path is further defined from the internal lumen into an interior proximal extension. In such aspects, the proximal extension may further define an outflow opening to further define the outflow path from the interior of the proximal extensions through the outflow opening.

Another end effector assembly of a tissue-resecting device provided in accordance with aspects of the present disclosure includes an outer shaft, a driver wire, a distal cutting tip, a hub housing, and a driver. The outer shaft defines a proximal end portion and a distal end portion defining a window therethrough. The drive wire extends through the outer shaft and defines a proximal end portion and a distal end portion. The proximal end portion of the drive wire includes a longitudinally-extending segment and a finger disposed at an angle relative to a longitudinally-extending segment. The distal cutting tip is disposed within the outer shaft, engaged with the distal end portion of the drive wire, and at least partially overlaps the window. The hub housing is engaged with the proximal end portion of the outer shaft. The driver is disposed within the hub housing, and defines a longitudinally-extending slot and a transverse slot disposed in communication with the longitudinally-extending slot at an angle relative thereto. The longitudinally-extending slot is configured to receive the longitudinally-extending segment of the drive wire and the transverse slot configured to receive the finger of the drive wire to thereby engage the driver with the proximal end portion of the drive wire. The driver is configured to be driven to rotate relative to the hub housing to thereby rotate the drive wire and distal cutting tip within and relative to the outer shaft.

In an aspect of the present disclosure, the finger is disposed at about a 90 degree angle relative to the longitudinally-extending segment and the transverse slot is disposed at about a 90 degree angle relative to the longitudinally-extending slot.

In another aspect of the present disclosure, the outer shaft includes a cutting edge surrounding the window. The cutting edge defines a plurality of cutting teeth.

In still another aspect of the present disclosure the distal cutting tip defines a mouth in communication with the window in at least one rotational orientation of the distal cutting tip relative to the outer shaft. In such aspects, the distal cutting tip may include a plurality of teeth disposed along opposing sides of the mouth.

In yet another aspect of the present disclosure, adhesive between at least one of the longitudinally-extending slot and the longitudinally-extending segment or the transverse slot and the finger further secures engagement of the driver with the proximal end portion of the drive wire.

In still yet another aspect of the present disclosure, the driver is overmolded about the proximal end portion of the drive wire to thereby define the longitudinally-extending slot receiving the longitudinally-extending segment and the transverse slot receiving the finger and engage the driver about the proximal end portion of the drive wire.

In another aspect of the present disclosure, the driver defines first and second lateral openings on either side of the longitudinally-extending slot and disposed in communication with an internal lumen of the driver.

Another end effector assembly of a tissue-resecting device provided in accordance with aspects of the present disclosure includes an outer shaft, a drive wire, a distal cutting tip, a hub housing, a driver, and a connector. The outer shaft defines a proximal end portion and a distal end portion defining a window therethrough. The drive wire extends through the outer shaft and defines a proximal end portion and a distal end portion. The distal cutting tip is disposed within the outer shaft, engaged with the distal end portion of the drive wire, and at least partially overlaps the window. The hub housing is engaged with the proximal end portion of the outer shaft. The driver is disposed within the hub housing and configured to be driven to rotate relative to the hub housing. The connector couples the proximal end portion of the drive wire with the driver such that rotation of the driver relative to the hub housing thereby rotates the drive wire and distal cutting tip within and relative to the outer shaft.

In an aspect of the present disclosure, the outer shaft includes a cutting edge surrounding the window. The cutting edge defines a plurality of cutting teeth.

In another aspect of the present disclosure the distal cutting tip defines a mouth in communication with the window in at least one rotational orientation of the distal cutting tip relative to the outer shaft. In such aspects, the distal cutting tip may include a plurality of teeth disposed along opposing sides of the mouth.

In still another aspect of the present disclosure, the connector is engaged with the proximal end portion of the drive wire in a first manner and is engaged with the driver in a second, different manner.

Also provided in accordance with aspects of the present disclosure is an end effector assembly of a tissue-resecting device including an outer shaft, a drive wire, and a distal cutting tip. The outer shaft has a proximal end portion and a distal end portion defining a window therethrough. The drive wire extends through the outer shaft and includes a cylindrical body and a distal end portion defining a semi-cylindrical configuration including a semi-cylindrical bottom surface and a planar top surface. A semi-cylindrical cut-out is defined within the planar upper surface. The distal cutting tip is disposed within the outer shaft and at least partially overlaps the window. The distal cutting tip has a semi-cylindrical lumen defined by a semi-cylindrical bottom surface and an open top. The distal end portion of the drive wire is at least partially received within the semi-cylindrical lumen of the distal cutting tip and engaged therein with the semi-cylindrical bottom surface of the distal end portion of the drive wire substantially mating with the semi-cylindrical bottom surface of the distal cutting tip. The drive wire is configured to drive rotation or oscillation of the distal cutting tip relative to the outer shaft.

In an aspect of the present disclosure, the distal cutting tip includes a plurality of teeth extending along a portion of a length thereof. The plurality of teeth includes a first set of teeth disposed on a first side of the semi-cylindrical lumen and a second set of teeth disposed on a second, opposite side of the semi-cylindrical lumen.

In another aspect of the present disclosure, a distal end of the distal end portion of the drive wire does not extend distally beyond a first tooth of each of the first and second sets of teeth. Alternatively or additionally, a distal end of the distal end portion of the drive wire is positioned proximally of the plurality of teeth.

In yet another aspect of the present disclosure, the drive wire includes a transition portion disposed between the cylindrical body and the distal end portion. The transition portion includes a curved surface. In such aspects, the semi-cylindrical cut-out may include a transition portion defined within the transition portion of the drive wire. The transition portion of the semi-cylindrical cut-out is defined by a curved bottom surface.

In still another aspect of the present disclosure, the distal end portion of the drive wire includes a beveled distal surface.

Another end effector assembly of a tissue-resecting device provided in accordance with the present disclosure includes an outer shaft, a drive wire, and a distal cutting tip. The outer shaft defines a proximal end portion and a distal end portion defining a window therethrough. The drive wire extends through the outer shaft and includes an at least partially cylindrical surface. The distal cutting tip is disposed within the outer shaft and at least partially overlaps the window. The distal cutting tip defines a semi-cylindrical lumen defined by a semi-cylindrical bottom surface and an open top. The distal cutting tip further includes a slot defined through the semi-cylindrical bottom surface. A distal end portion of the drive wire is at least partially received within the semi-cylindrical lumen of the distal cutting tip and engaged therein. The at least partially cylindrical surface extends at least partially into the slot. The drive wire is configured to drive rotation or oscillation of the distal cutting tip relative to the outer shaft.

In an aspect of the present disclosure, the drive wire includes a cylindrical body and the distal end portion of the drive wire defines a semi-cylindrical configuration including a semi-cylindrical bottom surface and a planar top surface. The semi-cylindrical bottom surface serves as the at least partially cylindrical surface extending at least partially into the slot.

In another aspect of the present disclosure, the drive wire includes a transition portion disposed between the cylindrical body and the distal end portion.

In still another aspect of the present disclosure, the planar top surface of the distal end portion of the drive wire is recessed relative to the open top of the distal cutting tip.

In yet another aspect of the present disclosure, the distal cutting tip includes a plurality of teeth extending along a portion of a length thereof. The plurality of teeth includes a first set of teeth disposed on a first side of the semi-cylindrical lumen and a second set of teeth disposed on a second, opposite side of the semi-cylindrical lumen.

Still yet another end effector assembly of a tissue-resecting device provided in accordance with aspects of the present disclosure includes an outer shaft, a drive wire, and a distal cutting tip. The outer shaft has a proximal end portion and a distal end portion defining a window therethrough. The drive wire extends through the outer shaft and defines a cylindrical configuration. The distal cutting tip is disposed within the outer shaft and at least partially overlaps the window. The distal cutting tip defines a semi-cylindrical lumen defined by a semi-cylindrical bottom surface and an open top. The drive wire extends distally into the distal cutting tip a distance of no more than 20% of a length of the distal cutting tip and is engaged therein. The drive wire is configured to drive rotation or oscillation of the distal cutting tip relative to the outer shaft.

In an aspect of the present disclosure, the drive wire extends distally into the distal cutting tip a distance of no more than 17% of the length of the distal cutting tip. In another aspect, the drive wire extends distally into the distal cutting tip a distance of no more than 15% of the length of the distal cutting tip.

In another aspect of the present disclosure, the distal cutting tip includes a plurality of teeth extending along a portion of a length thereof. The plurality of teeth includes a first set of teeth disposed on a first side of the semi-cylindrical lumen and a second set of teeth disposed on a second, opposite side of the semi-cylindrical lumen.

In yet another aspect of the present disclosure, a distal end of the drive wire is proximally-spaced from the plurality of teeth.

In still another aspect of the present disclosure, the drive wire is engaged within the cutting tip via lap welding or butt welding.

BRIEF DESCRIPTION OF THE DRAWINGS

Various aspects and features of the present disclosure are described hereinbelow with reference to the drawings wherein like numerals designate identical or corresponding elements in each of the several views.

FIG. 6 is an enlarged, perspective view of the area of detail indicated as "6" in FIG. 5;

FIG. 7 is an exploded, perspective view illustrating a drive wire, a cutting tip, and a portion of a drive assembly of the end effector assembly of FIG. 1;

FIG. 8 is an enlarged, perspective view of the area of detail indicated as "8" in FIG. 5;

FIG. 9 is an exploded, perspective view illustrating an outer shaft and a portion of a hub assembly of the end effector assembly of FIG. 1;

DETAILED DESCRIPTION

Figure 1:
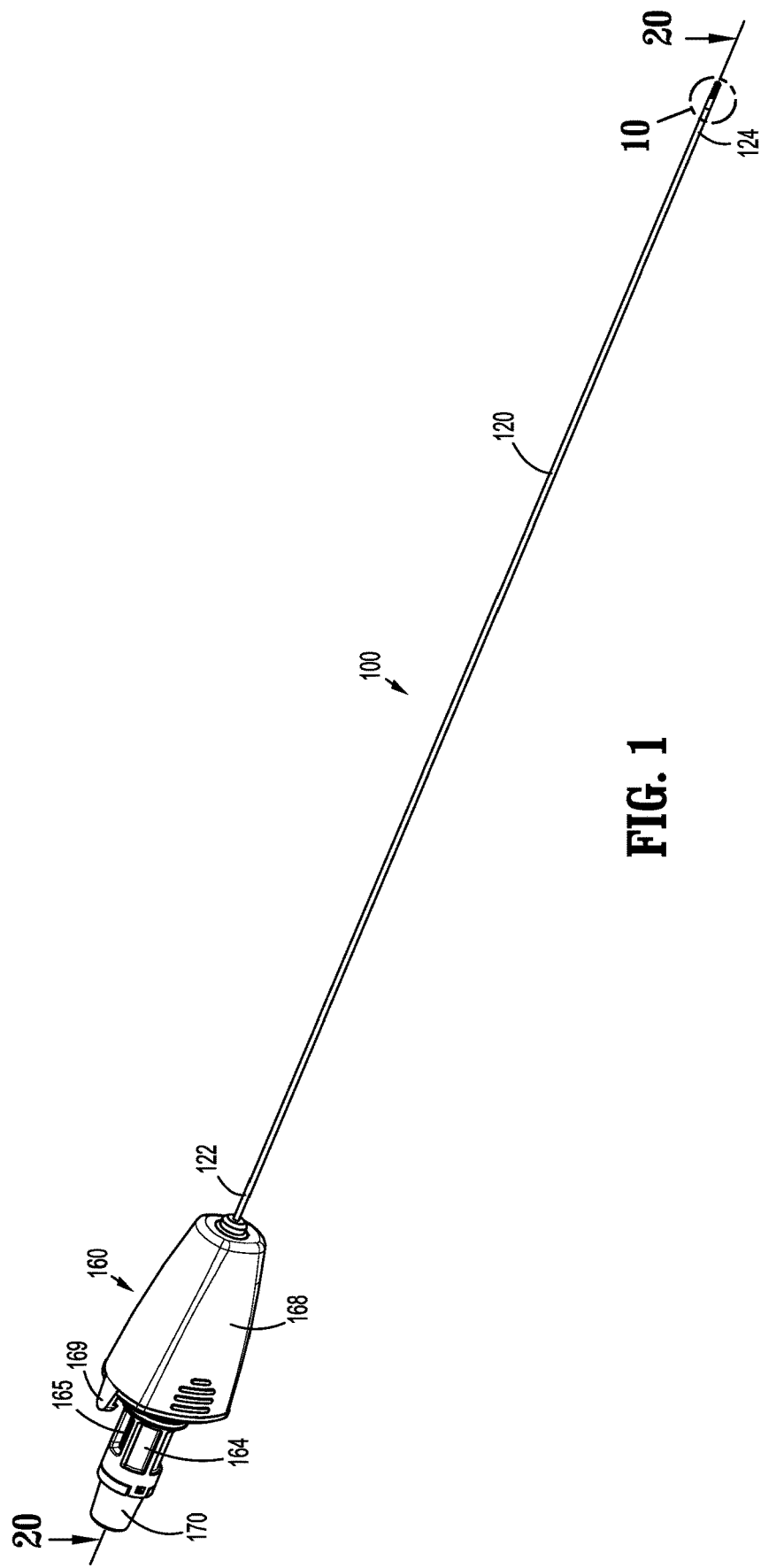
FIG. 1 is a perspective view of an end effector assembly of a tissue resecting instrument provided in accordance with aspects of the present disclosure.
Figure 2:
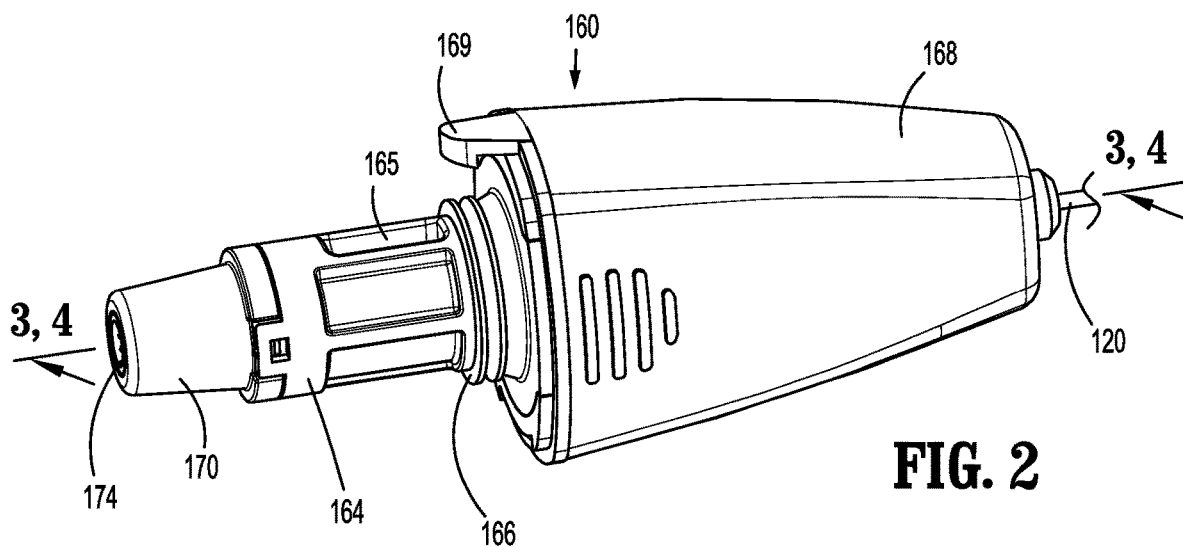
FIG. 2 is an enlarged, perspective view of a proximal end portion of the end effector assembly of FIG. 1.
Figure 3:
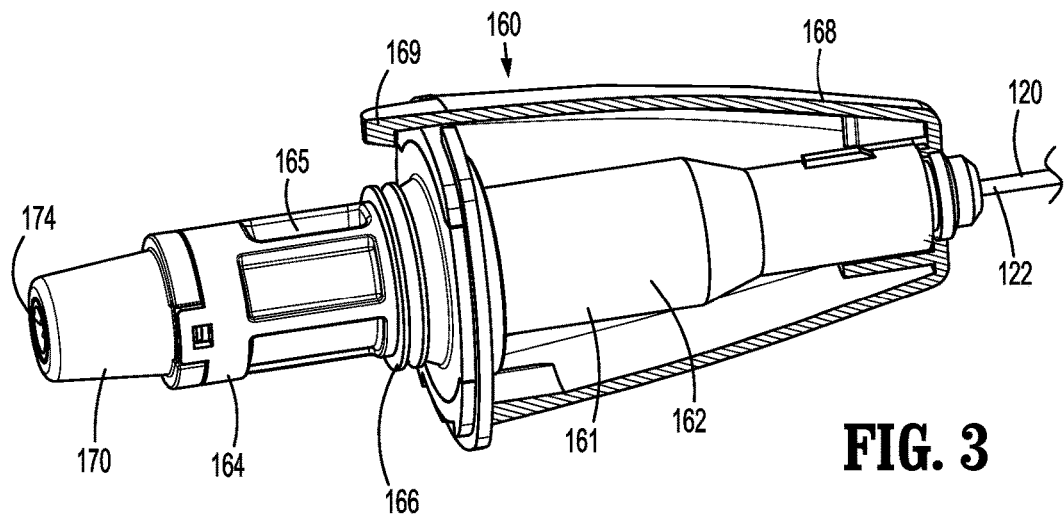
FIG. 3 is a partial, longitudinal, cross-sectional view taken across section line "3,4-3,4" of FIG. 2.
Figure 4:
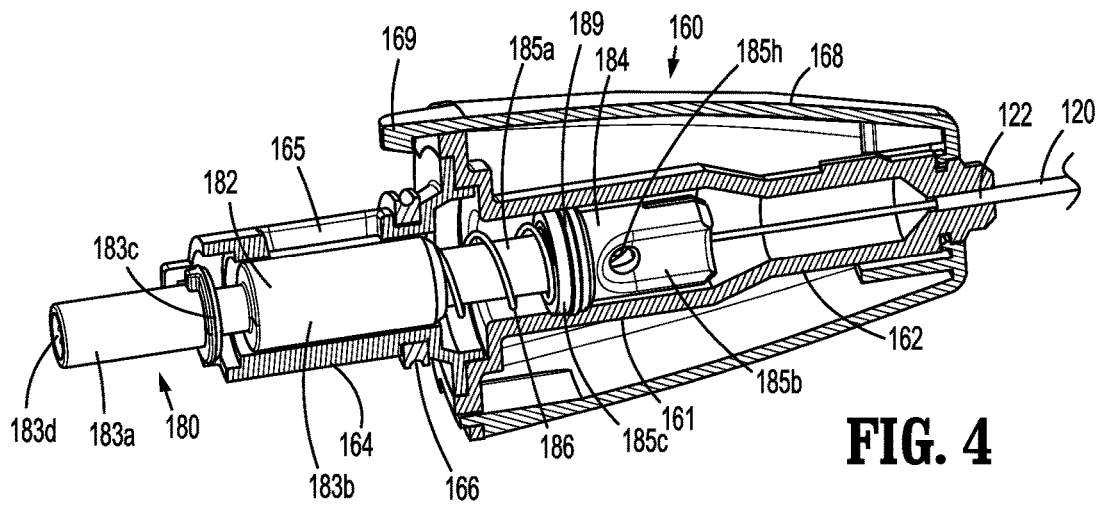
FIG. 4 is a longitudinal, cross-sectional view taken across section line "3,4-3,4" of FIG. 2.
Figure 23:
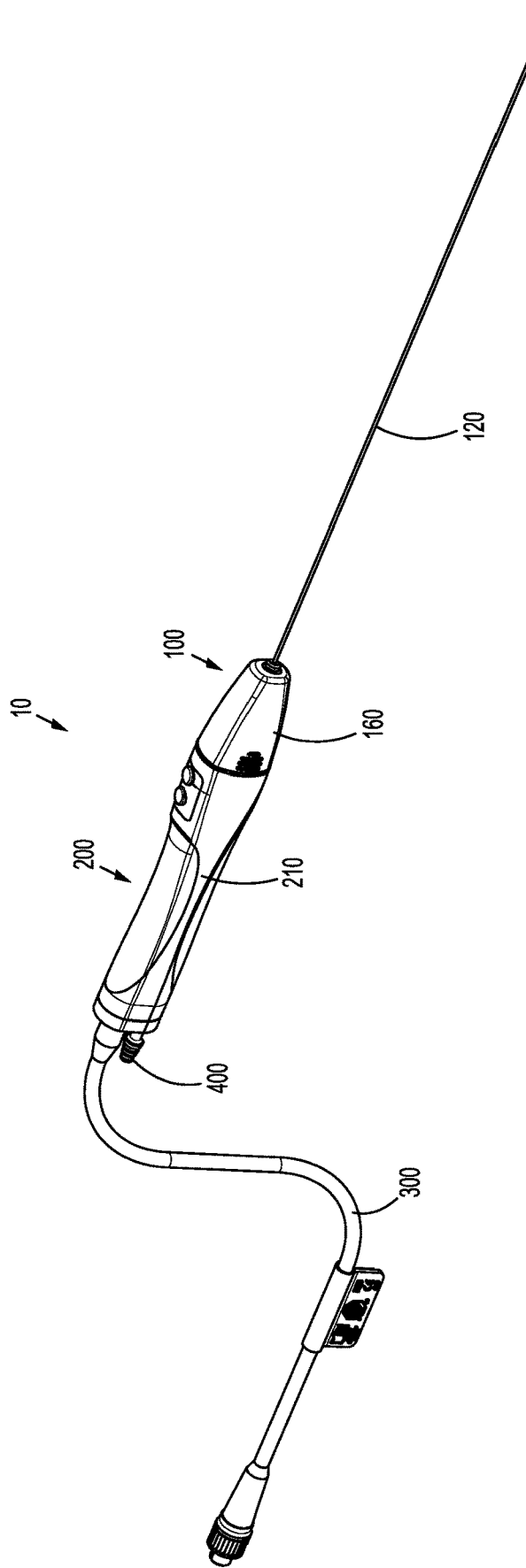
FIG. 23 is a perspective view of a tissue resecting instrument provided in accordance with aspects of the present disclosure including the end effector assembly of FIG. 1 engaged with a handpiece assembly.

Referring generally to FIGS. 1 and 23, a tissue resecting instrument 10 provided in accordance with the present disclosure and configured to resect tissue includes an end effector assembly 100 and a handpiece assembly 200. Tissue resecting instrument 10 is adapted to connect to a control unit (not shown) via a cable 300 to provide power and control functionality to tissue resecting instrument 10, although tissue resecting instrument 10 may alternatively or additionally include a power source, e.g., battery, and/or a control unit disposed within handpiece assembly 200. Tissue resecting instrument 10 is further adapted to connect to a fluid management system (not shown) via outflow tubing (not shown) connected to outflow port 400 for applying suction to remove fluid, tissue, and debris from a surgical site via tissue resecting instrument 10. The control unit and fluid management system may be integral with one another, coupled to one another, or separate from one another.

Tissue resecting instrument 10 may be configured as a single-use device that is discarded after use or sent to a manufacturer for reprocessing, a reusable device capable of being cleaned and/or sterilized for repeated use by the end-user, or a partially-single-use, partially-reusable device. With respect to partially-single-use, partially-reusable configurations, handpiece assembly 200 may be configured as a cleanable/sterilizable, reusable component, while end effector assembly 100 is configured as a single-use, disposable/reprocessable component. In any of the above configurations, end effector assembly 100 is configured to releasably engage handpiece assembly 200 to facilitate disposal/reprocessing of any single-use components and cleaning and/or sterilization of any reusable components. Further, enabling releasable engagement of end effector assembly 100 with handpiece assembly 200 allows for interchangeable use of different end effector assemblies, e.g., different length, configuration, etc., end effector assemblies, with handpiece assembly 200.

Figure 5:
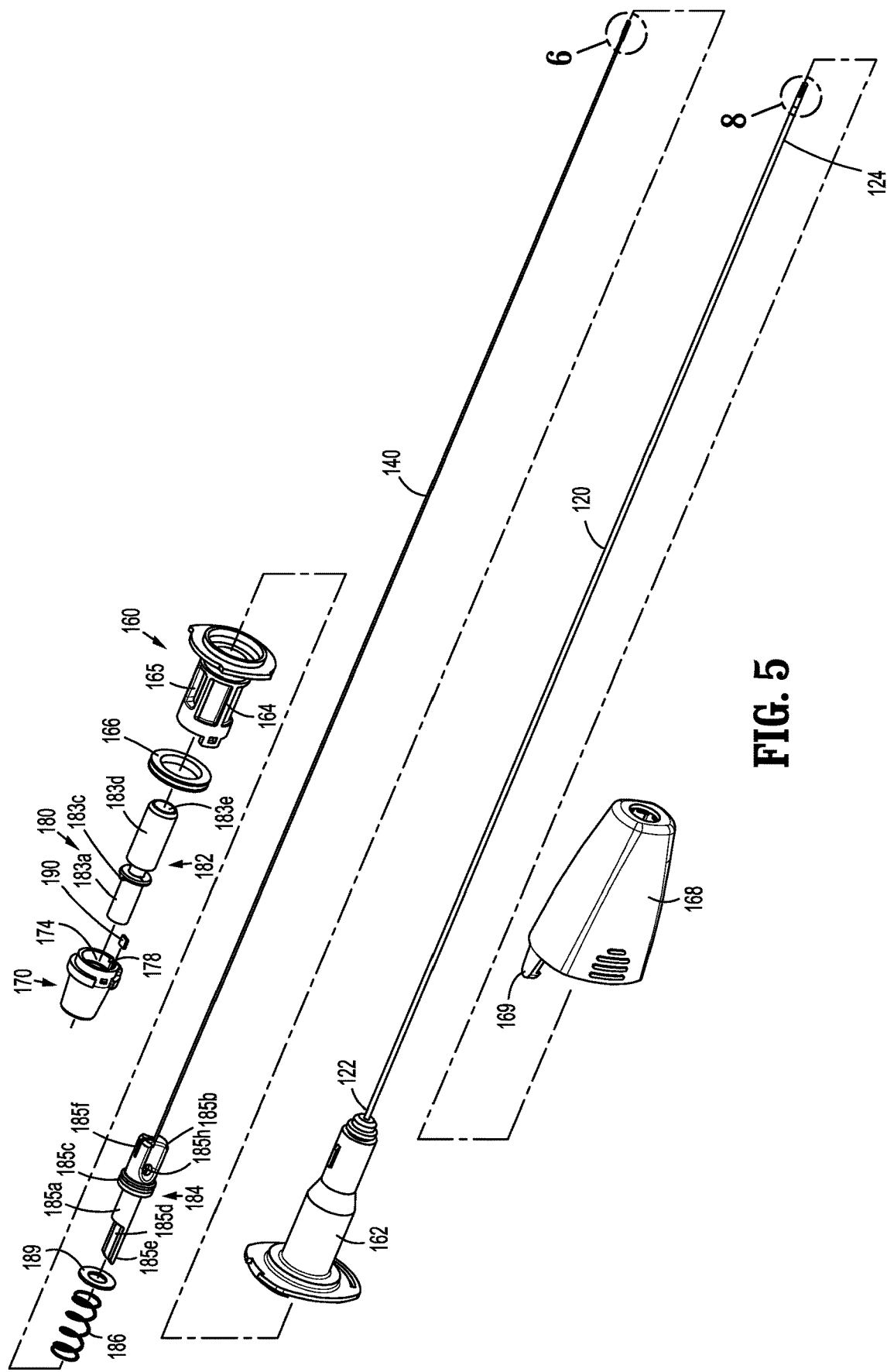
FIG. 5 is an exploded, perspective view of the end effector assembly of FIG. 1.

Continuing with reference to FIG. 1, end effector assembly 100 includes an outer shaft 120, a drive wire 140, a hub assembly 160, a drive assembly 180 (FIG. 5), and an RFID chip 190 (FIG. 5). Referring also to FIGS. 2-5, 8, and 9, outer shaft 120 includes a proximal end portion 122 and a distal end portion 124 defining an at least partially closed distal end 126 and a transverse window 128 disposed adjacent the at least partially closed distal end 126. Window 128 provides access to the interior of outer shaft 120 transversely through a sidewall thereof and may be surrounded by a cutting edge 129a extending about at least a portion of the outer perimeter of window 128 to facilitate cutting of tissue passing through window 128 and into outer shaft 120. Cutting edge 129a may define a serrated configuration including a plurality of cutting teeth 129b extending along longitudinal sides of cutting window 128 or may define any other suitable configuration. In embodiments, cutting teeth 129b are arcuate in configuration to conform to the tubular shape of outer shaft 120.

Outer shaft 120 may be formed as a single, monolithic piece of material or may be formed from multiple pieces that are formed separately and subsequently joined to one another. For example, outer shaft 120 may include an elongated cylindrical body portion 121a and a distal tip portion 121b (which includes at least partially closed distal end 126, window 128, and cutting edge 129a) joined to one another via laser welding or in any other suitable manner. Outer shaft 120 may be formed from stainless steel or other suitable material. Outer shaft 120 may define an outer diameter of, in embodiments, equal to or less than about 0.085 inches; in other embodiments, equal to or less than about 0.075 inches and, in still other embodiments, equal to or less than about 0.065 inches. Outer shaft 120 may define an inner diameter of, in embodiments, equal to or less than about 0.070 inches; in other embodiments, equal to or less than about 0.060 inches and, in still other embodiments, equal to or less than about 0.050 inches. "About" as utilized herein takes into account tolerances and variations generally accepted in the field, including but not limited to material, manufacturing, environmental, use, and measurement tolerances.

With reference to FIGS. 1-7, drive wire 140 is rotatably disposed within outer shaft 120 and includes a body 142 (FIG. 7) and a distal end portion 144. A proximal end portion 143a of body 142 of drive wire 140 is bent to define a finger 143b that, as detailed below, facilitates engagement of proximal end portion 143a of drive wire 140 within distal driver 184 of drive assembly 180, although other engagement configurations are also contemplated. Distal end portion 144 of drive wire 140 is at least partially received within and engaged with a distal cutting tip 150.

Referring to FIGS. 6 and 7, body 142 of drive wire 140 defines a cylindrical configuration having a substantially circular cross-section with an outer diameter of, in embodiments, equal to or less than about 0.045 inches; in other embodiments, equal to or less than about 0.035 inches and, in still other embodiments, equal to or less than about 0.025 inches. Material is removed from distal end portion 144 of drive wire 140 such that, rather than defining a circular cross-sectional configuration, distal end portion 144 defines a semi-circular cross-sectional configuration having a semi-cylindrical (semi-circular in cross-section) bottom surface 145a and a planar upper surface 145b. A transition section 146a defining an angled transition surface 146b is disposed between body 142 and distal end portion 144 of drive wire 140 to define a tapered transition between the radiused outer surface of body 142 and the planar upper surface 145b of distal end portion 144. Drive wire 140 may be formed as a solid rod of material, e.g., stainless steel, although other suitable materials and/or configurations are also contemplated.

Continuing with reference to FIGS. 6 and 7, as noted above, distal end portion 144 of drive wire 140 is at least partially received within and engaged with distal cutting tip 150. Distal cutting tip 150 includes a semi-cylindrical body 152 defining a semi-cylindrical lumen 154. Distal cutting tip 150 may be formed from any suitable material, e.g., stainless steel, and may be machined or otherwise formed. Semi-cylindrical body 152 defines a semi-cylindrical bottom surface 155a, a planar upper surface 155b, an open proximal end 155c, and an at least partially closed distal end 155d. Planar upper surface 155b is defined by first and second side walls 156 that are spaced apart from one another to define an elongated mouth 157 providing access to semi-cylindrical lumen 154 along the length thereof. Open proximal end 155c likewise provides access to semi-cylindrical lumen 154.

First and second side walls 156 may define a plurality of cutting teeth 158 protruding from (and/or defining valleys therebetween that are recessed from) planar upper surface 155b and extending along portions of the lengths of first and second side walls 156. With momentary reference to FIG. 10, cutting teeth 158 may be complementary to cutting teeth 129b such that, in one orientation of cutting tip 150 within outer shaft 120, the surfaces defined by cutting teeth 158 and cutting teeth 129b are fully aligned with one another, e.g., to appear as a single set of teeth. In embodiments, cutting teeth 158, like cutting teeth 129b, are arcuate in configuration to conform to the tubular shape of outer shaft 120 (where the radius defined by cutting teeth 158 is smaller than the radius defined by cutting teeth 129b since cutting teeth 158 are disposed radially inwardly of cutting teeth 129b).

Figure 10:
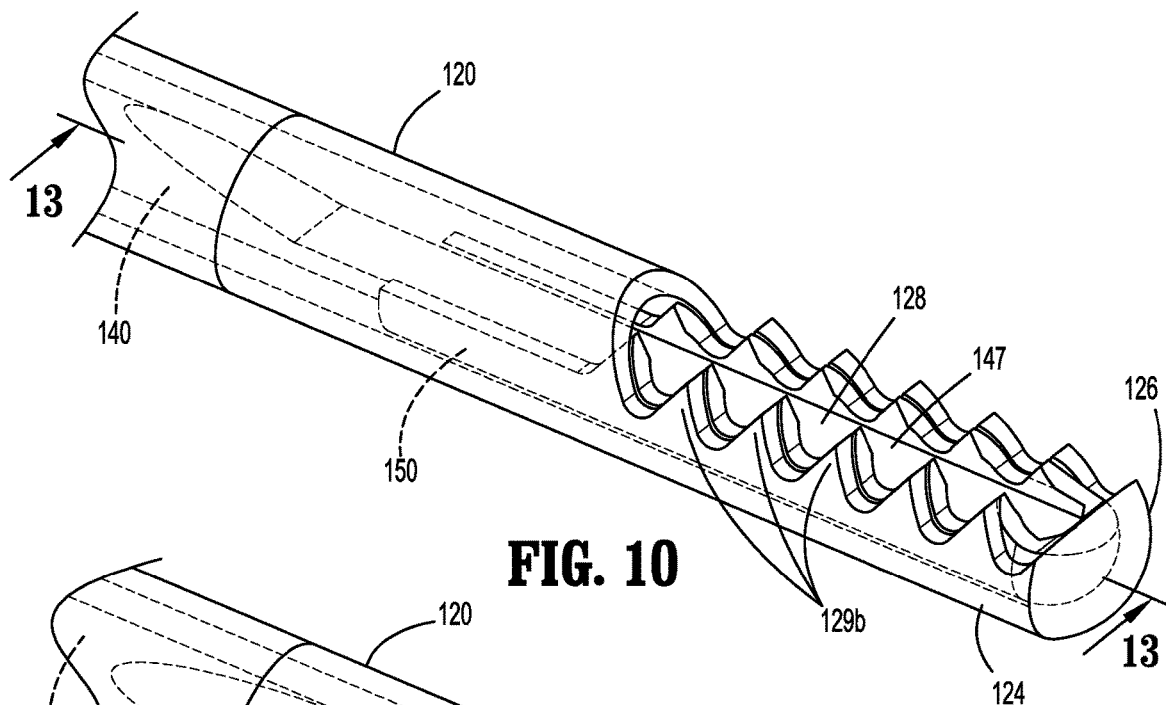
FIGS. 10-12 are enlarged, perspective views of the area of detail indicated as "10" in FIG. 1, illustrating rotation of the cutting tip within and relative to the outer shaft.
Figure 11:
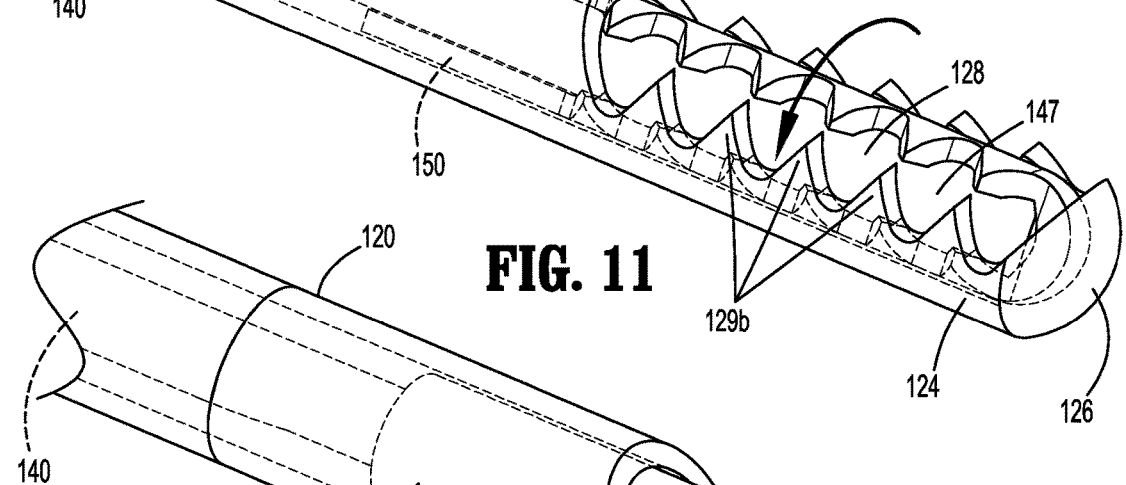
Figure 12:
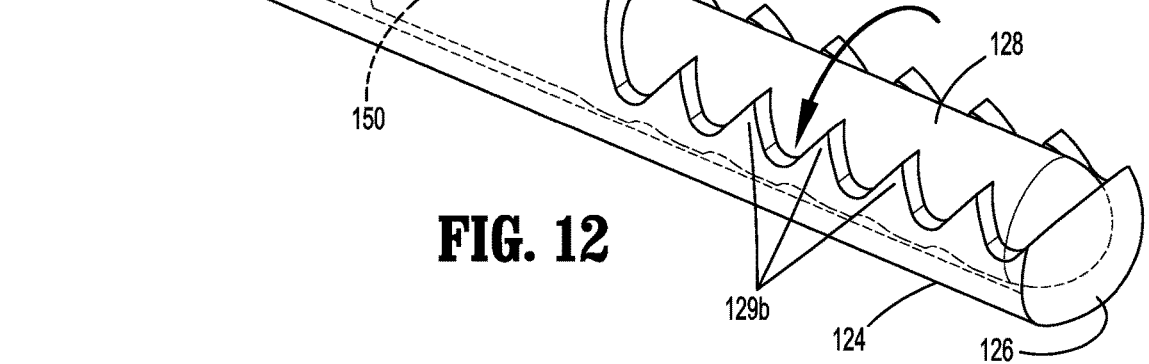
Figure 13:
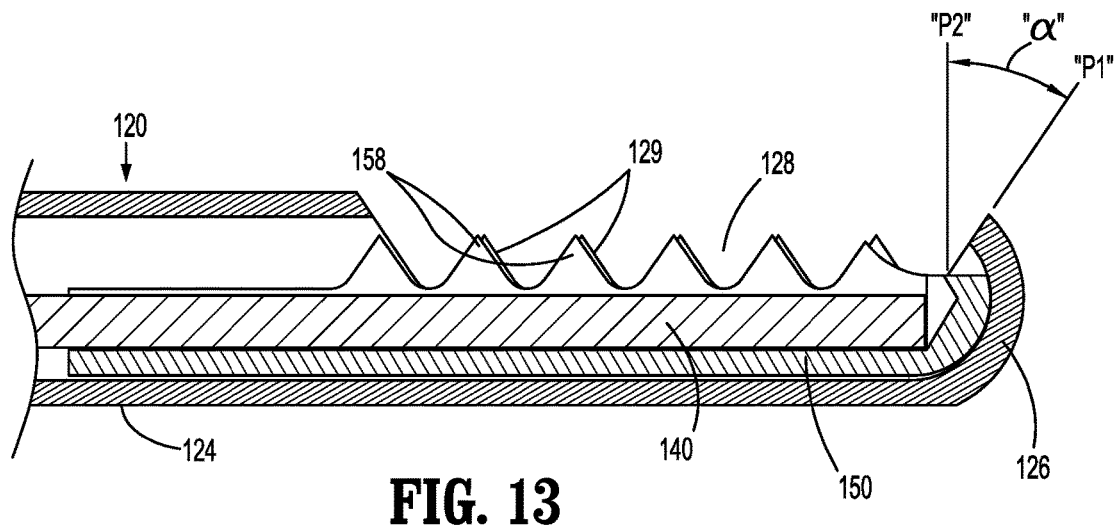
FIG. 13 is a longitudinal, cross-sectional view taken across section line "13-13" of FIG. 10.
Figure 14:
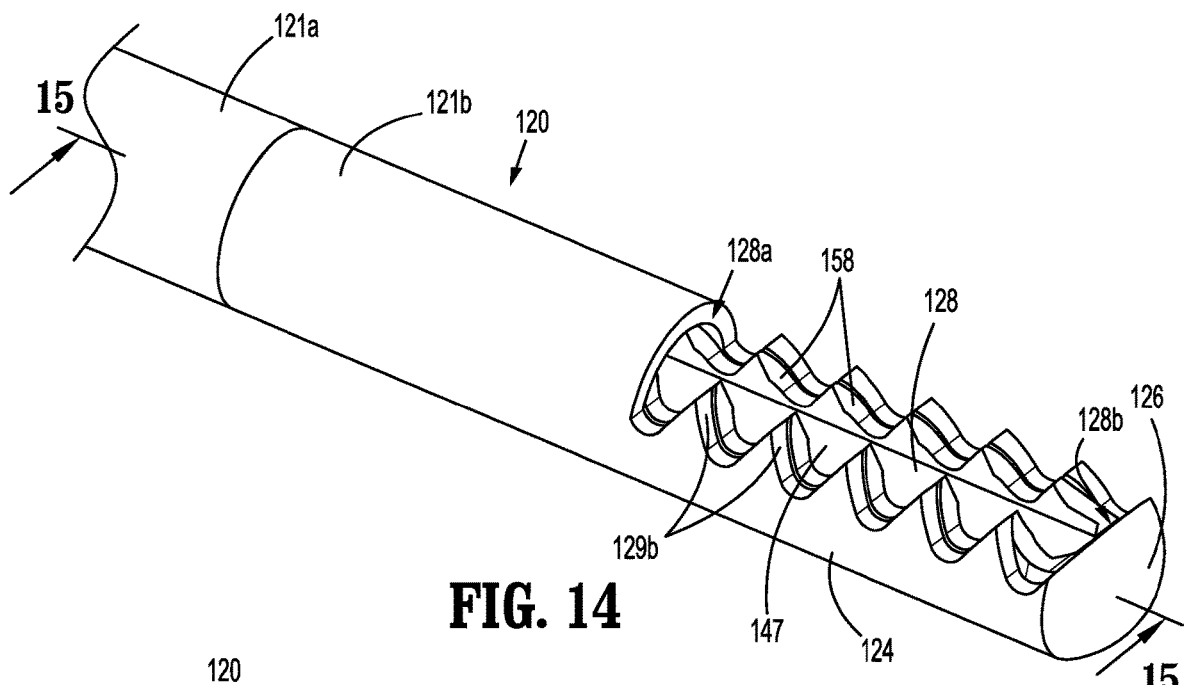
FIG. 14 is an enlarged, perspective view of another configuration of the distal end portion of the end effector assembly of FIG. 1.
Figure 15:
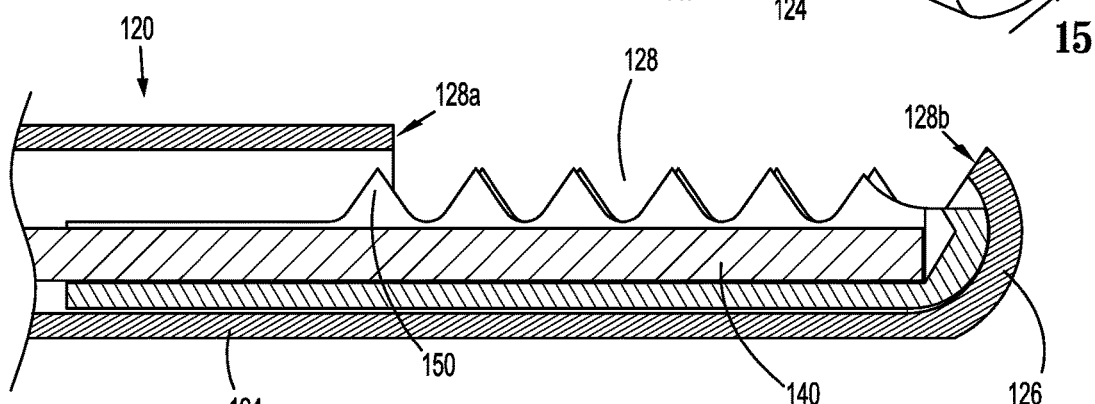
FIG. 15 is a longitudinal, cross-sectional view taken across section line "15-15" of FIG. 14.

Turning back to FIGS. 6 and 7, cutting tip 150, in embodiments, may define an outer diameter (e.g., of semi-cylindrical body 152) of, in embodiments, equal to or less than about 0.070 inches; in other embodiments, equal to or less than about 0.060 inches and, in still other embodiments, equal to or less than about 0.050 inches. An inner diameter of cutting tip 150 (e.g., of semi-cylindrical lumen 154) may be, in embodiments, equal to or less than about 0.055 inches; in other embodiments, equal to or less than about 0.045 inches and, in still other embodiments, equal to or less than about 0.035 inches. Referring also to FIGS. 10-12, the annular clearance defined between the outer diameter of cutting tip 150 and the inner diameter of outer shaft 120 may be, in embodiments, from about 0.001 inches to about 0.006 inches; and, in other embodiments from about 0.003 to about 0.004 inches.

With reference again to FIGS. 6 and 7, as noted above, distal end portion 144 of drive wire 140 is at least partially received within and engaged with distal cutting tip 150. More specifically, distal end portion 144 of drive wire 140 is received within semi-cylindrical lumen 154 such that the outer, semi-cylindrical bottom surface 145a of distal end portion 144 of drive wire 140 mates, complementarily, with the semi-cylindrical interior surface of cutting tip 150 that defines the semi-cylindrical bottom of semi-cylindrical lumen 154. In this position, planar upper surface 145*b* of distal end portion 144 of drive wire 140 may be co-planar with upper surface 155*b* (defined by side walls 156) of cutting tip 150. In order to secure distal end portion 144 of drive wire 140 within distal cutting tip 150 in this position, the abutting edges of planar upper surface 145*b* and upper surface 155*b* (defined by side walls 156) may be welded (e.g., via laser welding) or otherwise attached to one another on both sides thereof. The attachment, e.g., weld, locations may be proximal of cutting teeth 129*b*, 158 and/or any other suitable location(s).

Referring to FIGS. 10-12, drive wire 140 is configured for rotation or oscillation within and relative to outer shaft 120 to thereby rotate or oscillate distal cutting tip 150 relative to window 128. More specifically, inner shaft 140 is configured to rotate or oscillate between a first, open position (FIG. 10), a second, partially-closed position (FIG. 11), and a third, closed position (FIG. 12). In the first position, as illustrated in FIG. 10, cutting teeth 129*b*, 158 are aligned with one another and elongated mouth 157 is aligned with window 128 to enable maximum fluid communication therebetween. In the second position, as illustrated in FIG. 11, cutting teeth 129*b*, 158 are misaligned with one another (wherein only the teeth 158 on one side of distal cutting tip 150 are exposed) and elongated mouth 157 is misaligned with window 128 to enable only partial fluid communication therebetween. In the third position, as illustrated in FIG. 12, cutting teeth 129*b*, 158 are offset about 180 degrees relative to one another or in any other suitable position such that cutting teeth 158 are not exposed. Likewise, elongated mouth 157 and window 128 are offset about 180 degrees relative to one another or in any other suitable position such that fluid communication therebetween is substantially inhibited. With respect to rotational embodiments, drive wire 140 may be rotated in a single direction from the first position, to the second position, to the third position, and back to the first position (and may rotation continuously to repeat the same). With respect to oscillatory embodiments, drive wire 140 may be rotated in a first direction from the first position, to the second position, to the third position, and then in a second, opposite direction from the third position, to the second position, back to the first position (and may then return in the first direction in the same manner or may continue in the second direction to the third position before returning to the first position and repeating the same). Other oscillatory patterns and/or combinations of rotation and oscillation (e.g., where multiple revolutions are performed before switching directions) are also contemplated.

Figure 16:
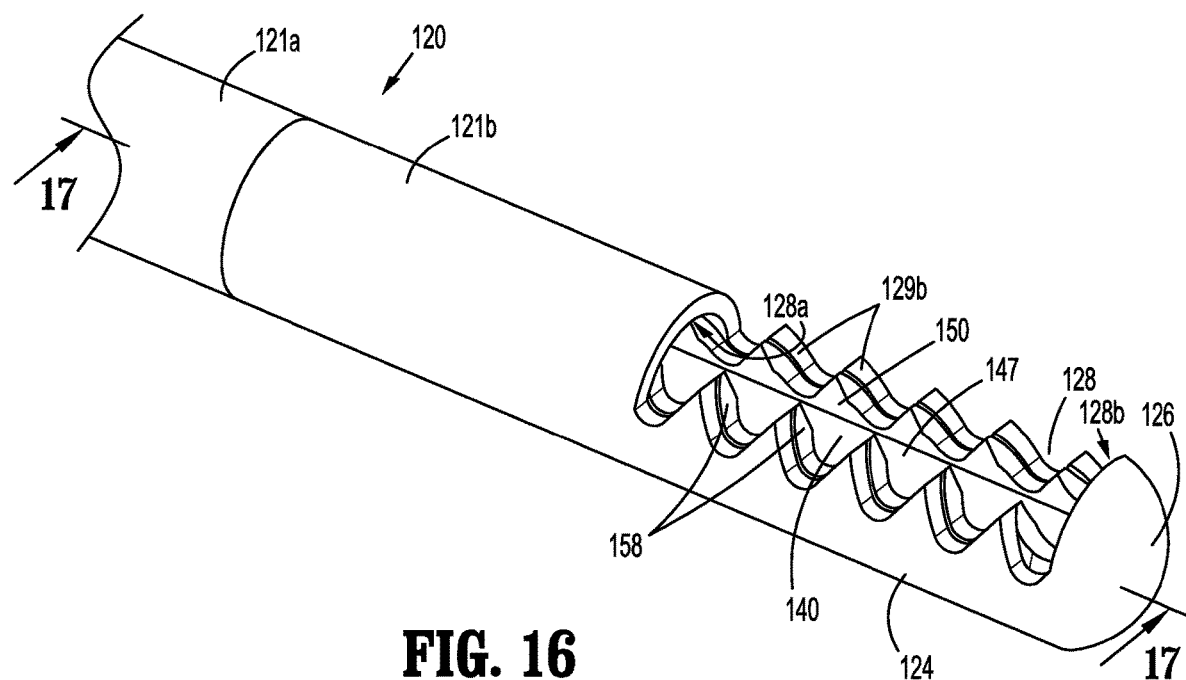
FIG. 16 is an enlarged, perspective view of yet another configuration of the distal end portion of the end effector assembly of FIG. 1.
Figure 17:
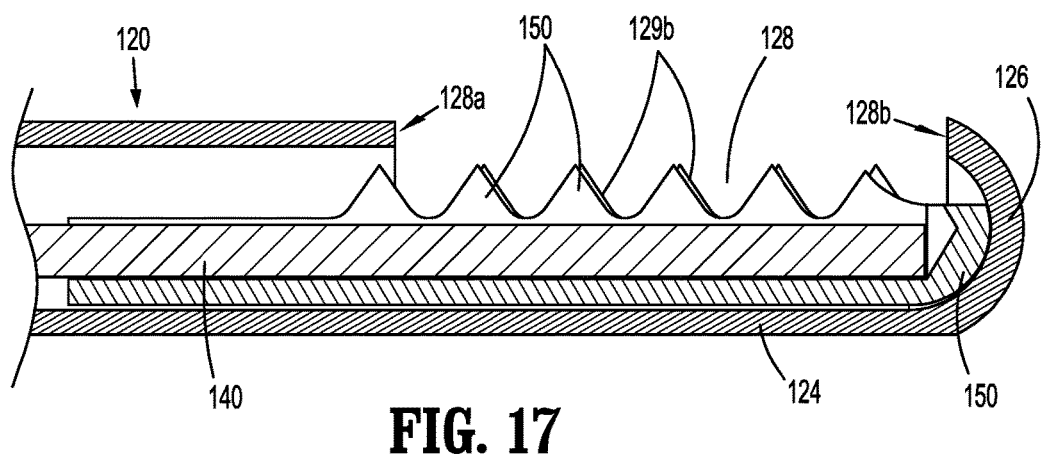
FIG. 17 is a longitudinal, cross-sectional view taken across section line "17-17" of FIG. 16.

Turning to FIGS. 10 and 13-15, in embodiments, either or both of the proximal and distal surfaces 128*a*, 128*b* of outer shaft 120 that define the longitudinal boundaries of window 128 may define a plane "P1" disposed at an angle "α" relative to a plane "P2" (vertically in the orientation illustrated in FIG. 13) which extends perpendicularly relative to a longitudinal axis of outer shaft 120. Plane "P1" defined by proximal and/or distal surfaces 128*a*, 128*b* may be angled longitudinally away from window 128 (e.g., wherein proximal surface 128*a* is angled proximally away from window 128 in a radially outward direction and/or distal surface 128*b* is angled distally away from window 128 in a radially outward direction). Angle "α" may be, in embodiments, from about 25 degrees to about 55 degrees; in other embodiments, from about 30 degrees to about 50; and, in other embodiments, from about 35 degrees to about 45 degrees. Alternatively, as illustrated in FIGS. 16 and 17, either or both of the proximal and distal surfaces 128*a*, 128*b* of outer shaft 120 may define a plane that extends perpendicularly relative to the longitudinal axis of outer shaft 120. In any of the above embodiments, distal cutting tip 150 may extend distally beyond window 128 to facilitation constraining distal cutting tip 150 within outer shaft 120. Additionally or alternatively, one or more of the proximal-most cutting teeth 158 of distal cutting tip 150 may be at least partially disposed proximal of window 128.

In the embodiments of FIGS. 10 and 13-15, distal end 126 of outer shaft 120 is partially closed in that distal end 126 does not extend about a full 180 degrees but, rather, extends 180 minus "α" degrees. In the embodiment of FIGS. 16 and 17, on the other hand, distal end 126 of outer shaft 120 is fully closed in that it extends about a full 180 degrees (e.g., wherein "α" is equal to about 0 degrees).

Figure 18:
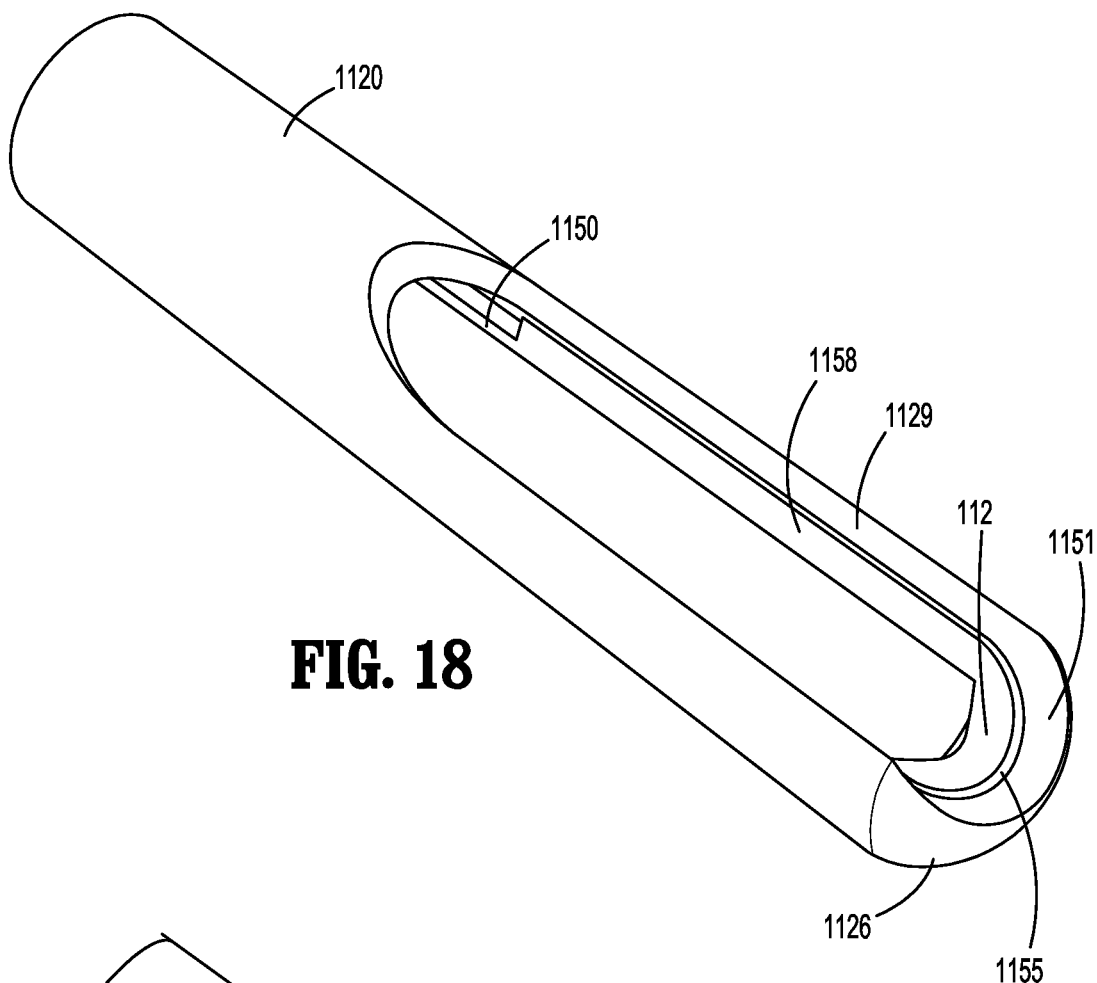
FIG. 18 is an enlarged, perspective view of a distal end portion of another end effector assembly provided in accordance with aspects of the present disclosure.

Turning to FIG. 18, in embodiments, rather than providing teeth, both outer shaft 1120 and distal cutting tip 1150 may define a generally planar cutting edge 1129, 1158, respectively. In such embodiments, distal ends 1126, 1155*d* of outer shaft 1120 and distal cutting tip 1150, respectively, may be only partially closed and include respective U-shaped openings 1121, 1151 defined therein. Cutting edge 1129, 1158 may extend about U-shaped openings 1121, 1151 or U-shaped openings 1121, 1151 may be defined by blunt surfaces.

Figure 19:
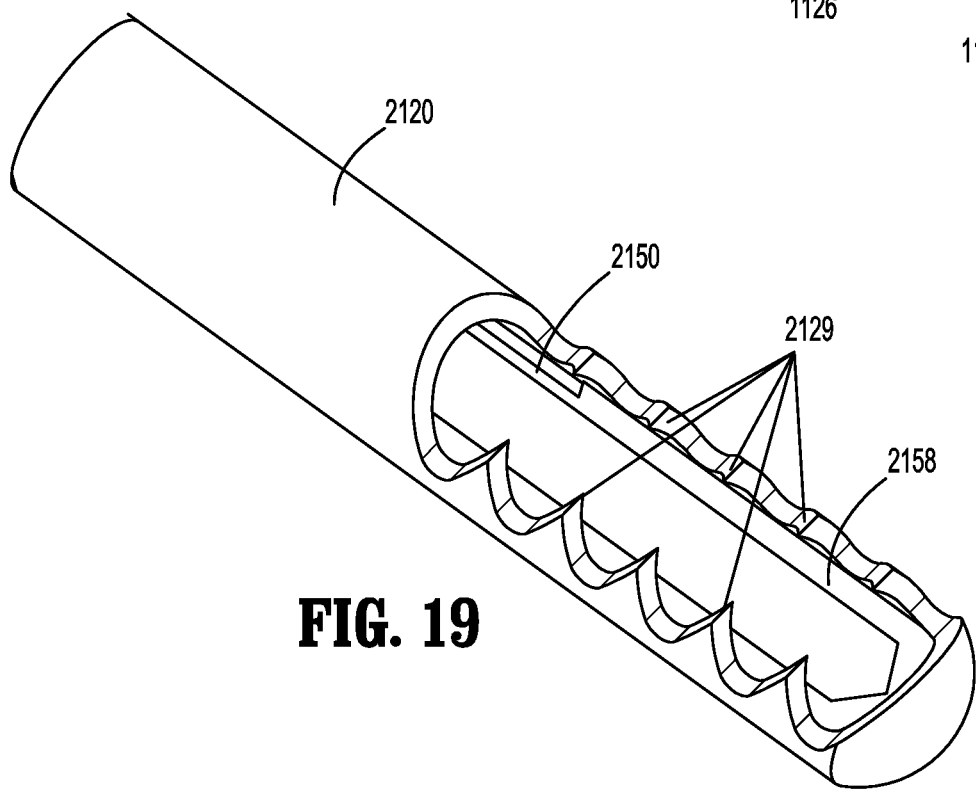
FIG. 19 is an enlarged, perspective view of a distal end portion of still yet another end effector assembly provided in accordance with aspects of the present disclosure.

As shown in FIG. 19, in other embodiments, rather than both including teeth, one of outer shaft 2120 and distal cutting tip 2150, e.g., distal cutting tip 2150, may define a generally planar cutting edge 2158 while the other of outer shaft 2120 and distal cutting tip 2150, e.g., outer shaft 2120, defines teeth 2129. The reverse configuration is also contemplated.

With reference to FIGS. 1-5, as noted above, end effector assembly 100 includes outer shaft 120, drive wire 140, a hub assembly 160, and a drive assembly 180. End effector assembly 100 further includes an RFID chip 190 captured between a retainer cap 170 of hub assembly 160 and a proximal extension portion 164 of a hub housing 161 of hub assembly 160, as detailed below.

Hub assembly 160 includes a hub housing 161 having a distal body portion 162 and a proximal extension portion 164 that are configured for engagement with one another, e.g., via snap-fitting or other suitable engagement. With additional momentary reference to FIG. 23, with end effector assembly 100 engaged with handpiece assembly 200, proximal extension portion 164 of hub housing 161 extends into handpiece assembly 200 while distal body portion 162 substantially abuts and extends distally from handpiece assembly 200. Proximal extension portion 164 of hub housing 161 further defines an outflow opening 165 through a sidewall thereof that is configured to fluidly communicate with an internal bore (not shown) of handle housing 210 of handpiece assembly 200 when end effector assembly 100 is engaged therewith.

Returning to FIGS. 1-5 and 9, distal body portion 162 of hub housing 161 is fixedly disposed about proximal end portion 122 of outer shaft 120 with outer shaft 120 extending distally therefrom. Drive wire 140 extends through outer shaft 120, as noted above, and extends proximally through distal body portion 162 of hub housing 161 into proximal extension portion 164 of hub housing 161 wherein drive assembly 180 is operably coupled to finger 143*b* of proximal end portion 143*a* of body 142 of drive wire 140.

Figure 20:
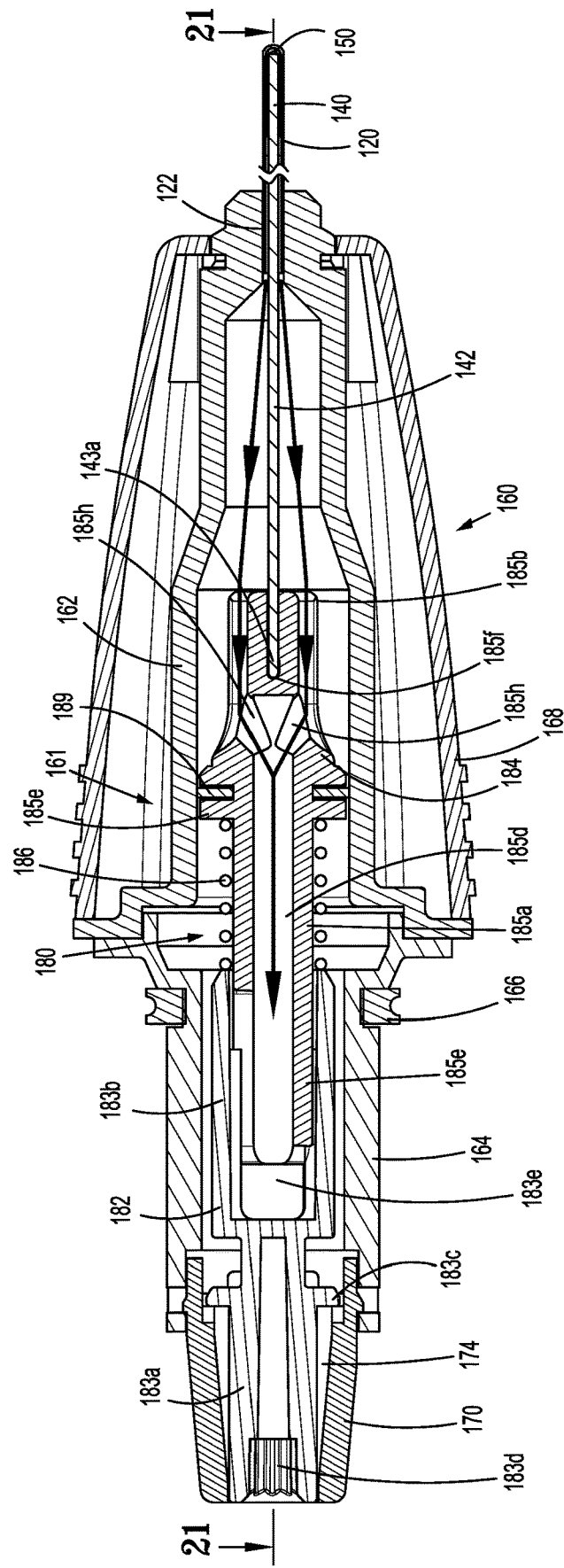
FIG. 20 is a longitudinal, cross-sectional view taken across section line "20-20" of FIG. 19.

Hub assembly 160 further includes an O-ring 166 configured for engagement about proximal extension portion 164 of hub housing 161 distally of outflow opening 165 (see FIG. 20). O-ring 166, is configured to establish a fluid-tight seal against the interior of handle housing 210 of handpiece assembly 200 (see FIG. 23) when end effector assembly 100 is engaged therewith to inhibit fluid from travelling distally after exiting outflow opening 165.

Hub assembly 160 additionally includes an outer shell 168 configured for positioning about distal body portion 162 of hub housing 161 and for engagement therewith, e.g., via snap-fit engagement or in any other suitable manner. A cantilever engagement finger 169 extends proximally from outer shell 168 of hub housing 161 and proximally from distal body portion 162 of hub housing 161 when outer shell 168 is engaged thereabout. Engagement finger 169 is configured for engagement within a corresponding aperture (not shown) defined within handle housing 210 of handpiece assembly 200 (see FIG. 23) to enable releasable engagement of end effector assembly 100 with handpiece assembly 200 (FIG. 23).

Continuing with reference to FIGS. 1-5, retainer cap 170 of hub assembly 160 is configured for snap-fit or other suitable engagement with a proximal end portion of proximal extension portion 164. Retainer cap 170 defines a longitudinal lumen 174 extending through retainer cap 170. Retainer cap 170 further defines a pocket 178 configured to receive RFID chip 190 therein. When retainer cap 170 is engaged with proximal extension portion 164, e.g., via snap-fitting, the open end of pocket 178 is blocked by a proximal face of proximal extension portion 164, thereby capturing RFID chip 190 therein.

Drive assembly 180 is configured to operably couple a drive rotor (not shown) of handpiece assembly 200 (see FIG. 23) with drive wire 140 such that rotation of the drive rotor drives rotation and/or oscillation of drive wire 140, thereby driving the rotation and/or oscillation of distal cutting tip 150 within and relative to outer shaft 120. Drive assembly 180, more specifically, includes a proximal driver 182, a distal driver 184, and a biasing spring 186, e.g., a coil compression spring. Additionally, drive assembly 180 may include gearing (not shown) configured to amplify or attenuate the output rotation of drive wire 140 relative to the input rotation received from the drive rotor of handpiece assembly 200 (FIG. 23).

Referring to FIG. 7, distal driver 184 of drive assembly 180 includes a proximal body portion 185a, a distal body portion 185b, and a collar 185c disposed between proximal and distal body portions 185a, 185b, respectively. A seal 189 may be engaged annularly about collar 185c. Seal 189 is configured to establish a fluid-tight seal across the annular gap between distal driver 184 and distal body portion 162 of hub housing 161 to inhibit fluid flow within the annular gap proximally beyond seal 189 (see FIG. 20). Distal drier 184 further includes a lumen 185d extending partially therethrough. Proximal body portion 185a of distal driver 184 further includes a proximal foot 185e extending proximally therefrom. At least a portion of proximal foot 185e defines a non-circular cross-sectional configuration, e.g., a semicircular, rectangular or other polygonal configuration. Further, lumen 185d is open at proximal foot 185e, e.g., proximal foot 185e defines an open portion in communication with lumen 185d.

Figure 21:
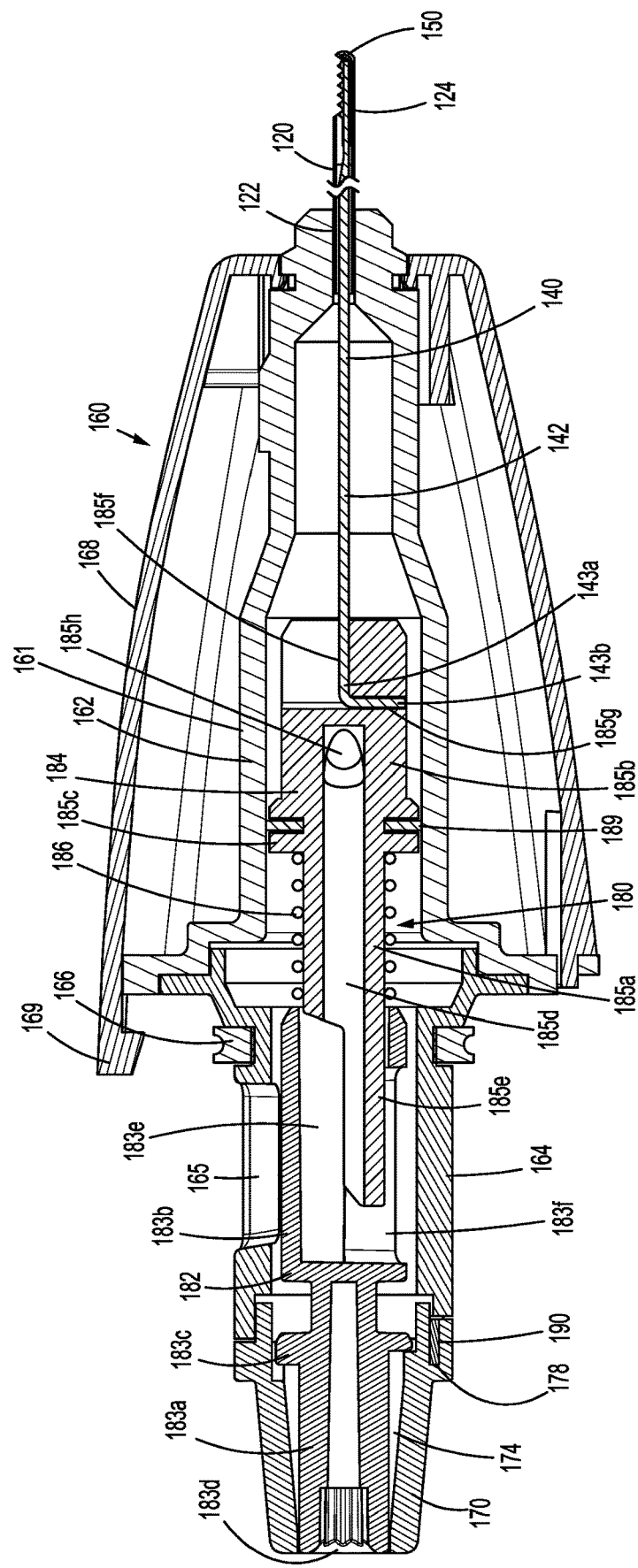
FIG. 21 is a longitudinal, cross-sectional view taken across section line "21-21" of FIG. 20.

Referring also to FIG. 21, distal body portion 185b of distal driver 184 of drive assembly 180 is configured to receive and engage finger 143b of proximal end portion 143a of body 142 of drive wire 140. More specifically, distal body portion 185b defines a longitudinally-extending slot 185f communicating with a transverse slot 185g. Transverse slot 185g is configured to receive finger 143b while longitudinally-extending slot 185f is configured to receive a portion of body 142 of drive wire 140 extending distally from finger 143b. Finger 143b may be disposed at about a right angle relative to body 142 or at any other suitable angle and, thus, transverse slot 185g may be disposed at about a right angle relative to longitudinally-extending slot 185f or at any other suitable angle. This right angle engagement facilitates torque transmission and provides axial securement between distal driver 184 and drive wire 140. Further, an adhesive (e.g., epoxy) disposed within transverse slot 185g and/or longitudinally-extending slot 185f (and/or on finger 143b and/or body 142) may be utilized to facilitate the engagement between distal driver 184 and drive wire 140. Instead of or in addition to the above-detailed transverse-finger (and adhesive) engagement, in embodiments, distal driver 184 is overmolded about proximal portion 143a of body 142 of drive wire 140 to secure distal driver 184 and drive wire 140 with one another.

Figure 22:
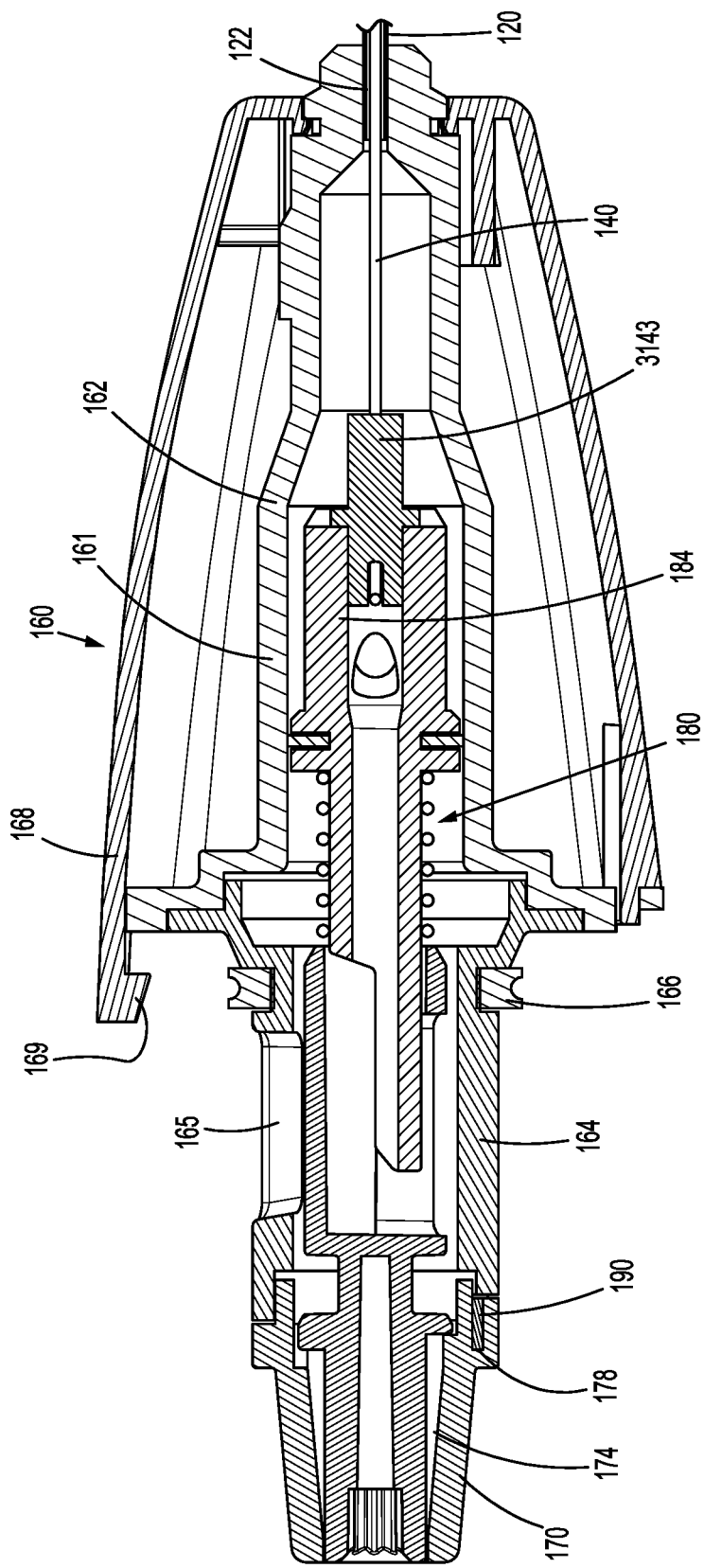
FIG. 22 is a longitudinal, cross-sectional view of another configuration for engaging a drive wire with a distal driver of the end effector assembly of FIG. 1.

As shown in FIG. 22, as an alternative to direct engagement of drive wire 140 with distal driver 184, a connector 3143 may be provided to engage drive wire 140 with distal driver 184. Drive wire 140 may be connected to connector 3143 via snap-fit engagement, adhesives (with or without a transverse-finger engagement as detailed above), press-fit engagement, heat staking, combinations thereof, or in any other suitable manner. Connector 3143, in turn, may be connected to distal drive 184 via spin welding, over-molding, heat staking, combinations thereof, or in any other suitable manner. Connector 3143 may be formed from a metal, e.g., stainless steel, a plastic, or may include both plastic and metal portions.

With reference to FIG. 20, distal driver 184 defines a flow path therethrough. More specifically, distal body portion 185b of distal driver 184 defines opposed lateral openings 185h on either side thereof that communication with lumen 185d of distal driver 184. In this manner, fluid, tissue, and debris that are suctioned through window 128 (FIGS. 10-12) and proximally through outer shaft 120 (about drive wire 140) into distal body portion 162 of hub housing 161 are further suctioned through lateral openings 185h and into lumen 185d.

Referring to FIGS. 4, 5, 20, and 21, proximal driver 182 of drive assembly 180 includes a proximal body portion 183a and a distal body portion 183b. Proximal body portion 183a includes an external collar 183c disposed annularly thereabout. Proximal body portion 183a further includes a proximally-facing cavity 183d at least a portion of which has a non-circular cross-sectional configuration, e.g., an 8-point star or other polygonal configuration, that is configured to at least partially receive the drive rotor of handpiece assembly 200 (FIG. 23) in fixed rotational orientation. Distal body portion 183b defines a distally-facing cavity 183e at least a portion of which has a non-circular cross-sectional configuration, e.g., a semicircular, rectangular, or other polygonal configuration. A longitudinally-extending slot 183f (FIG. 21) defined through a side wall of distal body portion 183b communicates with distally-facing cavity 183e. Distally-facing cavity 183e of distal body portion 183b of proximal driver 182 is configured to slidably receive proximal foot 185e of distal driver 184 in fixed rotational orientation due to the non-circular, and at least partially complementary, configurations thereof.

As illustrated in FIGS. 20 and 21, longitudinally-extending slot 183f of proximal driver 182 is disposed in fluid communication with lumen 185d of distal driver 184 such that fluid, tissue, and debris may be suctioned from lumen 18d, through longitudinally-extending slot 183f, and through outflow opening 165 of proximal extension portion 164 of hub housing 161 in at least some rotational orientations of proximal and distal drivers 182, 184, respectively, relative to hub housing 164. Fluid, tissue, and debris suctioned through outflow opening 165 of proximal extension portion 164 of hub housing 161 may further be suctioned through the outflow path defined through handle housing 210 of handpiece assembly 200 (FIG. 23) and, ultimately, through outflow port 400 (FIG. 23) and the outflow tubing (not shown) to a collection vessel (not shown). As understood, the suction may also be provided through the above-defined outflow path. More specifically, the outflow tubing (not shown) is configured to connect to outflow port 400 to thereby connect outflow port 400 to a fluid management system (not shown). The fluid management system includes a vacuum source to establish suction through tissue resecting instrument 10 and the outflow tubing to facilitate removal of fluid, tissue, and debris from the surgical site and may also include a collection reservoir, e.g., a collection canister, for collecting the removed fluid, tissue, and debris. As an alternative or in addition to a vacuum source establishing suction through tissue resecting instrument 10 and the outflow tubing, vacuum may be created therethrough via a pressure differential between the surgical site and the outflow path.

Referring again to FIGS. 4, 5, 20, and 21, biasing spring 186 is disposed about proximal body portion 185a of distal driver 184 and includes a distal end that abuts collar 185c of distal driver 184. Biasing spring 186 includes a proximal end that is configured to abut a distal end of distal body portion 183b of proximal driver 182. In this manner, biasing spring 186 biases proximal driver 182 proximally relative to distal driver 184. Complementary features on proximal driver 182 and retainer cap 170 may mate in this more-proximal position of proximal driver 182 to rotationally lock proximal and distal drivers 182, 184 relative to retainer cap 170 and hub housing 161 and, as a result, rotationally fix drive wire 140 relative to outer shaft 120 in this position. Upon engagement of end effector assembly 100 with handpiece assembly 200 (FIG. 23), the drive rotor (not shown, or other portion) of handpiece assembly 200 is received within proximally-facing cavity 183d of proximal body portion 183a of proximal driver 182 in fixed rotational orientation thereof, e.g., due to the at least partially complementary configurations thereof. As the driver rotor is inserted within proximally-facing cavity 183d and bottoms out therein, further insertion of end effector assembly 100 urges proximal driver 182 distally through and relative to retainer cap 170, against the bias of biasing spring 186, to thereby displace proximal driver 182 distally relative to retainer cap 170, displacing the complementary features and thereby rotationally unlocking proximal and distal drivers 182, 184 from retainer cap 170 and hub housing 161. Thus, upon engagement of end effector assembly 100 with handpiece assembly 200, drive wire 140 is unlocked from outer shaft 120 and permitted to rotate relative thereto.

Referring to FIGS. 21 and 23, with end effector assembly 100 engaged with handpiece assembly 200 as detailed above, RFID chip 190 of end effector assembly 100 is disposed in vertical registration with an RFID transceiver (not shown) of handpiece assembly 200 to enable the RFID transceiver to read/write data to/from RFID chip 190 and/or communicate read/write data to/from the control unit, e.g., via cable 300.

The data stored on RFID chip 190 of end effector assembly 100 may include item number, e.g., SKU number; date of manufacture; manufacture location, e.g., location code; serial number; use count (which may be updated by writing data from RFID transceiver 290 to RFID chip 190); the home/initial position of drive wire 140; the rotation type (rotation versus oscillation); RPM settings (default, high, medium, low); max RPM; pressure setting information; vacuum setting information; outflow setting information; calibration information; and/or encryption key(s). Additional or alternative data is also contemplated.

With general reference to FIGS. 1-5, 10-12, 20, 21, and 23, with end effector assembly 100 engaged with handpiece assembly 200 as detailed above, tissue resecting instrument 10 is ready for use. In use, the motor (not shown) of handpiece assembly 200 is activated to drive rotation of the drive rotor. Upon activation of the motor, with a head-start or delay relative to activation of the motor, or independently thereof, suction is established through tissue resecting instrument 10, e.g., via activating the vacuum source of the fluid management system.

Activation of the motor, in either a rotating or oscillating fashion, drives rotation of the drive rotor which, in turn, drives rotation of proximal driver 182 to, in turn, drive rotation of distal driver 184 and thereby rotate or oscillate drive wire 140 and, thus, distal cutting tip 150 relative to outer shaft 120. The rotation or oscillation of distal cutting tip 150 relative to outer shaft 120, together with the suction applied through outer shaft 120, enables tissue to be drawn through cutting window 128, cut by distal cutting tip 150 and/or cutting edge 129a, and suctioned, along with fluids and debris, proximally through outer shaft 120 (about drive wire 140), drive assembly 180, through output opening 165 of proximal extension portion 164 of hub housing 161, and through the outflow path of handpiece assembly 200 to outflow port 400 for output to the collection reservoir of the fluid management system.

Referring to FIG. 23, as an alternative to handpiece assembly 200 configured for manual grasping and manipulation during use, tissue resecting instrument 10 may alternatively be configured for use with a robotic surgical system wherein handle housing 210 is configured to engage a robotic arm of the robotic surgical system. The robotic surgical system may employ various robotic elements to assist the surgeon and allow remote operation (or partial remote operation). More specifically, various robotic arms, gears, cams, pulleys, electric and mechanical motors, etc. may be employed for this purpose and may be designed with the robotic surgical system to assist the surgeon during the course of an operation or treatment. The robotic surgical system may include remotely steerable systems, automatically flexible surgical systems, remotely flexible surgical systems, remotely articulating surgical systems, wireless surgical systems, modular or selectively configurable remotely operated surgical systems, etc.

The robotic surgical system may be employed with one or more consoles that are next to the operating theater or located in a remote location. In this instance, one team of surgeons or nurses may prep the patient for surgery and configure the robotic surgical system with the surgical device disclosed herein while another surgeon (or group of surgeons) remotely controls the surgical device via the robotic surgical system. As can be appreciated, a highly skilled surgeon may perform multiple operations in multiple locations without leaving his/her remote console which can be both economically advantageous and a benefit to the patient or a series of patients.

The robotic arms of the robotic surgical system are typically coupled to a pair of master handles by a controller. The handles can be moved by the surgeon to produce a corresponding movement of the working ends of any type of surgical instrument (e.g., end effectors, graspers, knifes, scissors, cameras, fluid delivery devices, etc.) which may complement the use of the tissue resecting devices described herein. The movement of the master handles may be scaled so that the working ends have a corresponding movement that is different, smaller or larger, than the movement performed by the operating hands of the surgeon. The scale factor or gearing ratio may be adjustable so that the operator can control the resolution of the working ends of the surgical instrument(s).

Figure 24:
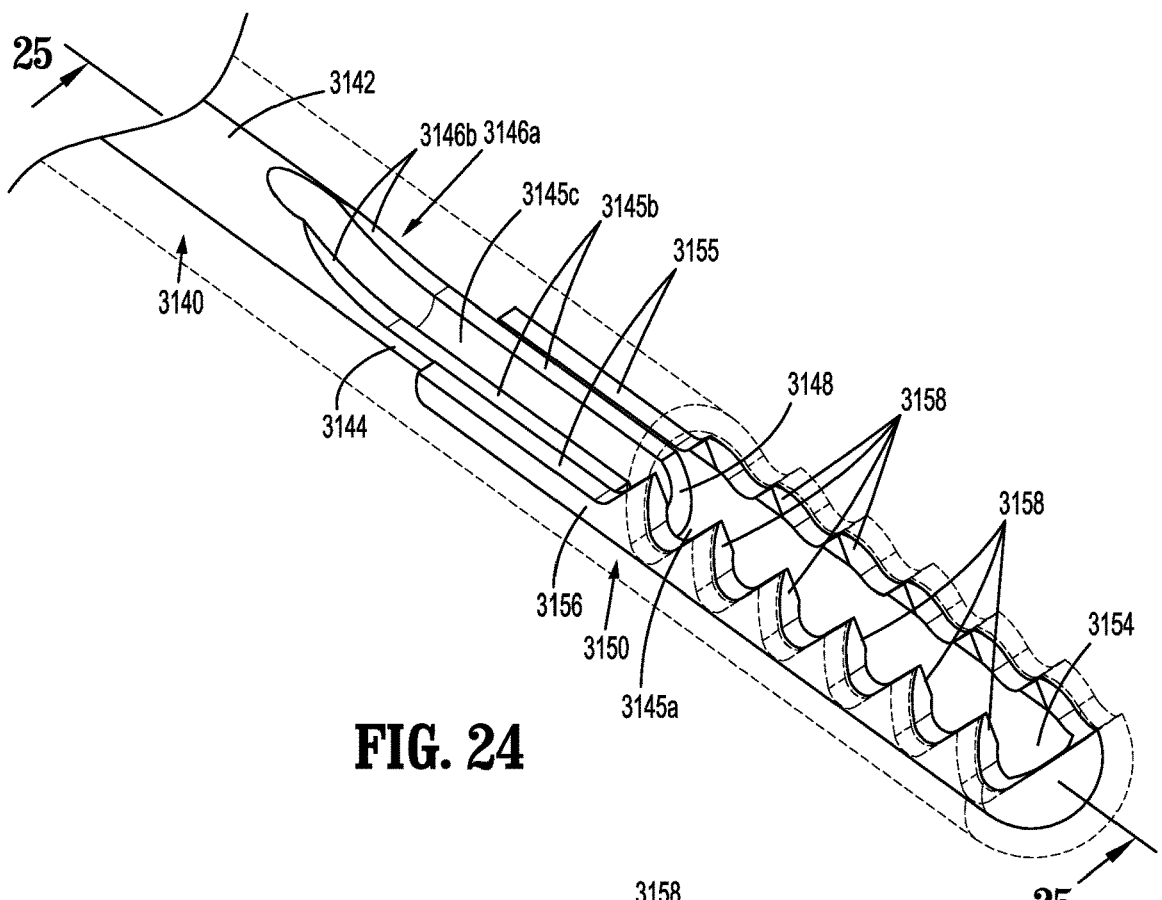
FIG. 24 is an enlarged, perspective view of still another configuration of the distal end portion of the end effector assembly of FIG. 1, with the outer shaft shown in phantom.
Figure 25:
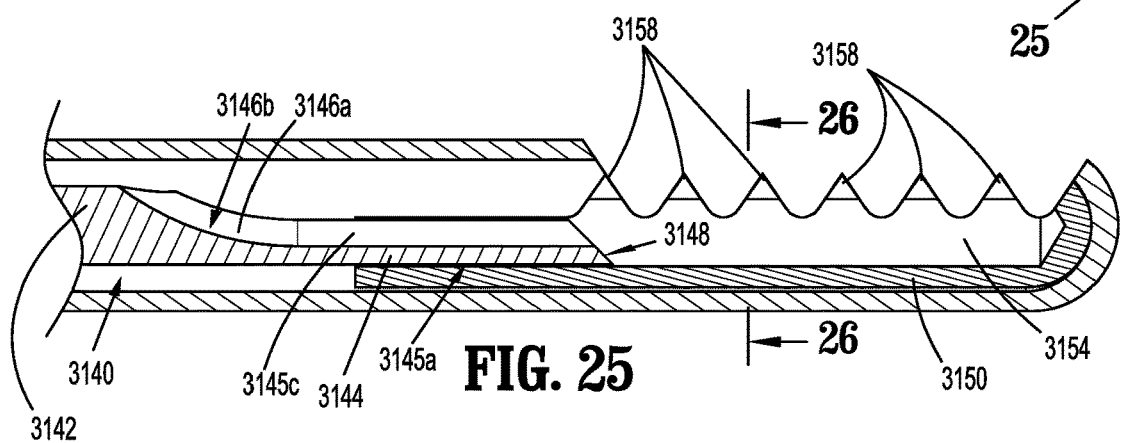
FIG. 25 is a longitudinal, cross-sectional view taken across section line "25-25" of FIG. 24.
Figure 26:
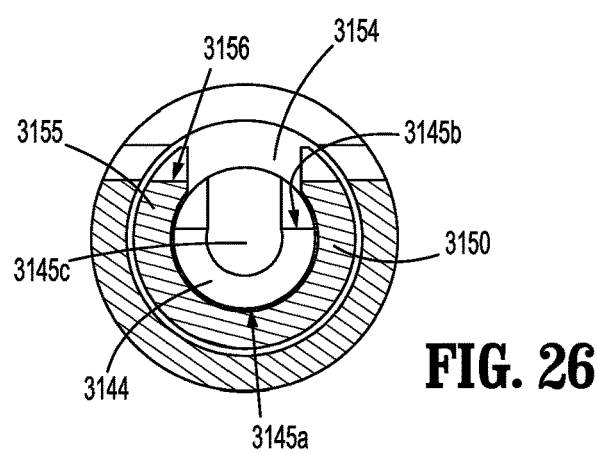
FIG. 26 is a transverse, cross-sectional view taken across section line "26-26" of FIG. 25.

Turning to FIGS. 24-26, another configuration of distal end portion 3144 of drive wire 3140, distal cutting tip 3150, and the engagement therebetween is shown. Except as specifically distinguished below, distal end portion 3144 of drive wire 3140, distal cutting tip 3150, and the engagement therebetween may be similar to any of the aspects detailed hereinabove. Distal end portion 3144 of drive wire 3140 has material removed therefrom such that, rather than defining a circular outer perimeter, distal end portion 3144 defines a semi-cylindrical (semi-circular in cross-section) bottom surface 3145a and a planar upper surface 3145b. A transition section 3146a defining a curved transition surface 3146b is disposed between body 3142 of drive wire 3140 and distal end portion 3144 of drive wire 3140 to define a smooth transition between the radiused outer surface of body 3142 and the planar upper surface 3145b of distal end portion 3144.

Distal end portion 3144 of drive wire 3140 further includes a semi-cylindrical cut-out 3145c defined therein and open to both the distal end of distal end portion 3144 of drive wire 3140 and planar upper surface 3145b such that planar upper surface 3145b is bifurcated into surface portions on either side of semi-cylindrical cut-out 3145c. Semi-cylindrical cut-out 3145c defines a substantially constant diameter along distal end portion 3144 and further includes a transition portion tapering (along a curved bottom surface) in depth in a distal-to-proximal direction to define a smooth transition from within semi-cylindrical cut-out 3145c to the exterior of body 3142 of drive wire 3140.

Distal end portion 3144 of drive wire 3140 is at least partially received within and engaged with distal cutting tip 3150. More specifically, distal end portion 3144 of drive wire 3140 is received within a proximal portion of semi-cylindrical lumen 3154 such that the outer, semi-cylindrical bottom surface 3145a of distal end portion 3144 of drive wire 3140 mates, complementarily, with the semi-cylindrical interior surface of cutting tip 3150 that defines the semi-cylindrical bottom of semi-cylindrical lumen 3154. Further, at least a portion of the distal end surface, e.g., beveled surface 3148, of distal end portion 3144 of drive wire 3140 is proximal of cutting teeth 3158 of distal cutting tip 3150 and/or the distal end surface of distal end portion 3144 of drive wire 3140 does not extend distally beyond the most-proximal tooth 3158 on either side of distal cutting tip 3150. The bifurcated planar upper surface 3145b of distal end portion 3144 of drive wire 3140 may be co-planar with upper surface 3155 (defined by side walls 3156) of cutting tip 3150.

The more-proximal positioning of distal end portion 3144 of drive wire 3140 relative to cutting tip 3150 maximizes the open volume within the portion of semi-cylindrical lumen 3154 underneath cutting teeth 3158 to increase the volume of tissue, fluids, and debris capable of being received therein. Semi-cylindrical cut-out 3145c, extending proximally from the portion of semi-cylindrical lumen 3154 underneath cutting teeth 3158, provides an additional open volume to facilitate the flow of tissue, fluids, and debris proximally through outer shaft 3120 about distal end portion 3144 of drive wire 3140. Further, the distal end of distal end portion 3144 of drive wire 3140 may define a beveled surface 3148 to facilitate the flow of tissue, fluid, and debris proximally from semi-cylindrical lumen 3154 into semi-cylindrical cut-out 3145c and/or about distal end portion 3144 of drive wire 3140.

Figure 27:
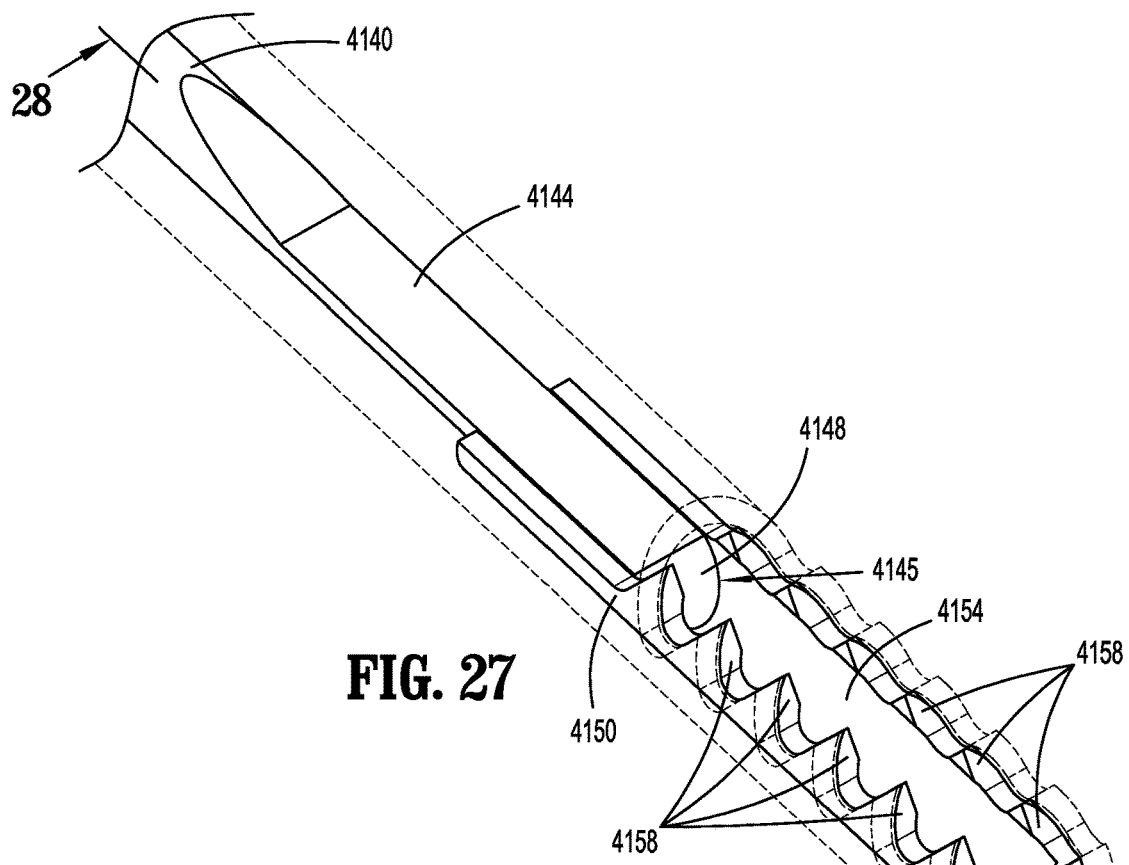
FIG. 27 is an enlarged, perspective view of yet another configuration of the distal end portion of the end effector assembly of FIG. 1, with the outer shaft shown in phantom.
Figure 28:
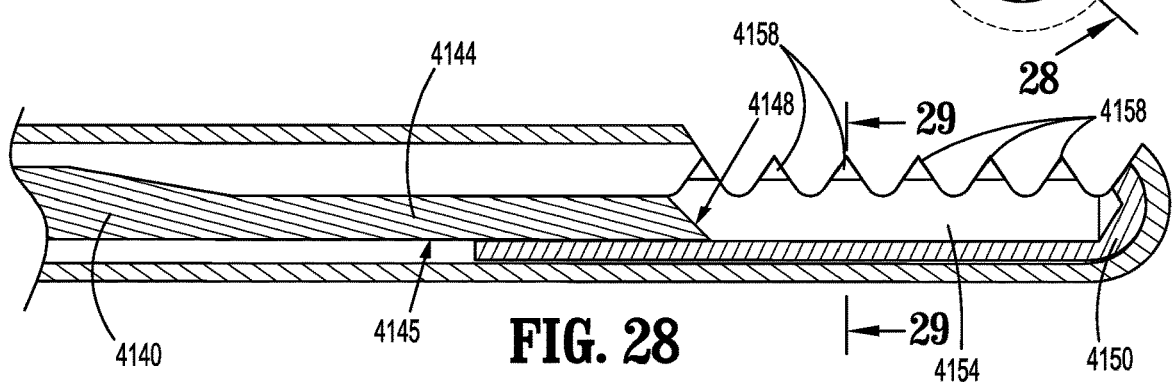
FIG. 28 is a longitudinal, cross-sectional view taken across section line "28-28" of FIG. 27.
Figure 29:
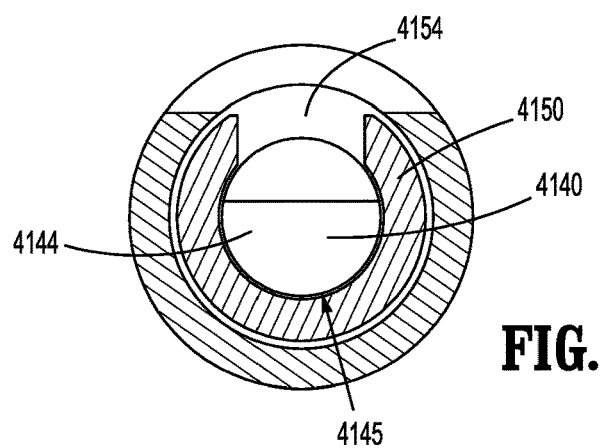
FIG. 29 is a transverse, cross-sectional view taken across section line "29-29" of FIG. 28.

With reference to FIGS. 27-29, another configuration of distal end portion 4144 of drive wire 4140, distal cutting tip 4150, and the engagement therebetween is shown. Except as specifically distinguished below, distal end portion 4144 of drive wire 4140, distal cutting tip 4150, and the engagement therebetween may be similar to any of the aspects detailed hereinabove. Distal end portion 4144 of drive wire 4140 is similar to distal end portion 3144 of drive wire 3140 (FIGS. 24-26) except that distal end portion 4144 does not include a semi-cylindrical cut-out. Distal end portion 4144 of drive wire 4140 is received within a proximal portion of semi-cylindrical lumen 4154 of cutting tip 4150 such that the outer, semi-cylindrical bottom surface 4145 of distal end portion 4144 of drive wire 4140 mates, complementarily, with the semi-cylindrical interior surface of cutting tip 4150 that defines the semi-cylindrical bottom of semi-cylindrical lumen 4154. Further, at least a portion of the distal end surface, e.g., beveled surface 4148, of distal end portion 4144 of drive wire 4140 is proximal of cutting teeth 4158 of distal cutting tip 4150 and/or the distal end surface of distal end portion 4144 of drive wire 4140 does not extend distally beyond the most-proximal tooth 4158 on either side of distal cutting tip 4150.

Figure 30:
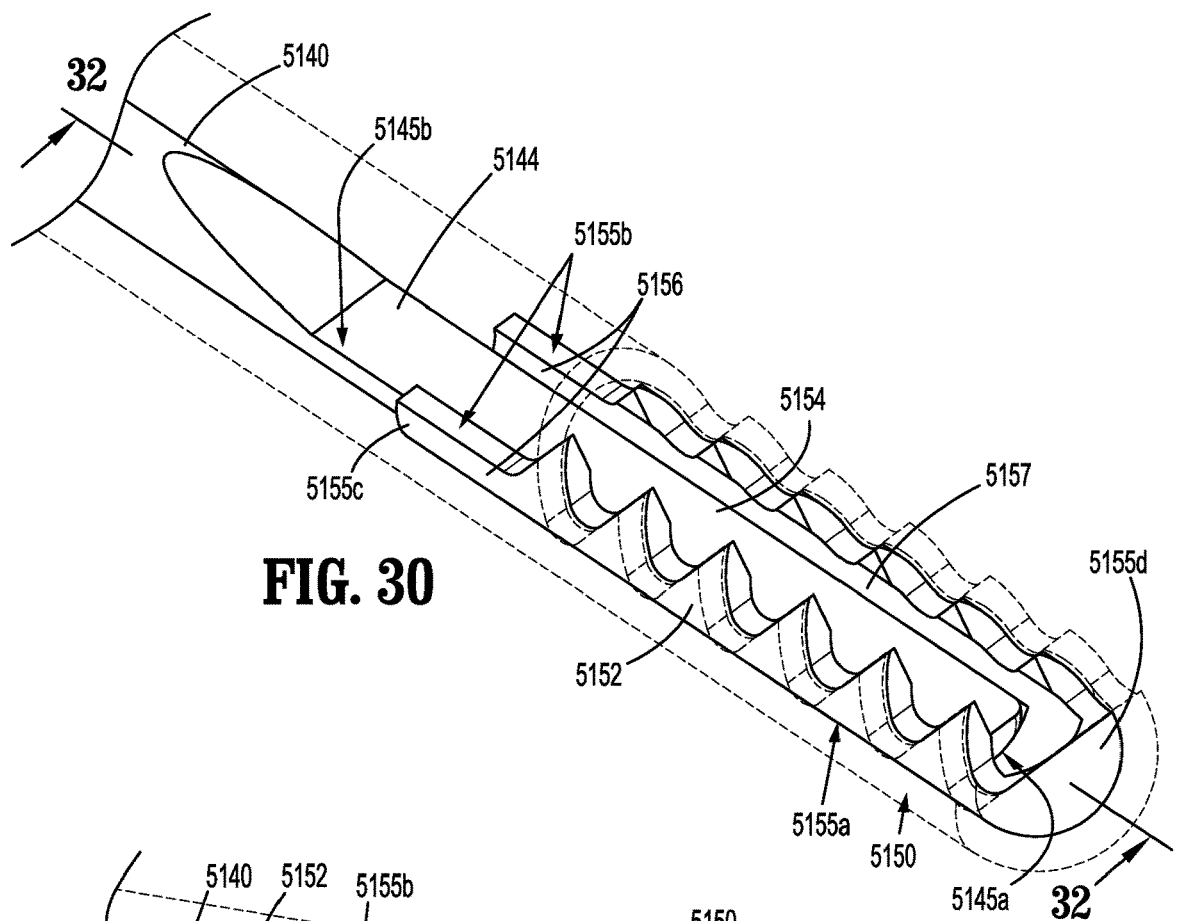
FIG. 30 is an enlarged, top, perspective view of still yet another configuration of the distal end portion of the end effector assembly of FIG. 1, with the outer shaft shown in phantom.
Figure 31:
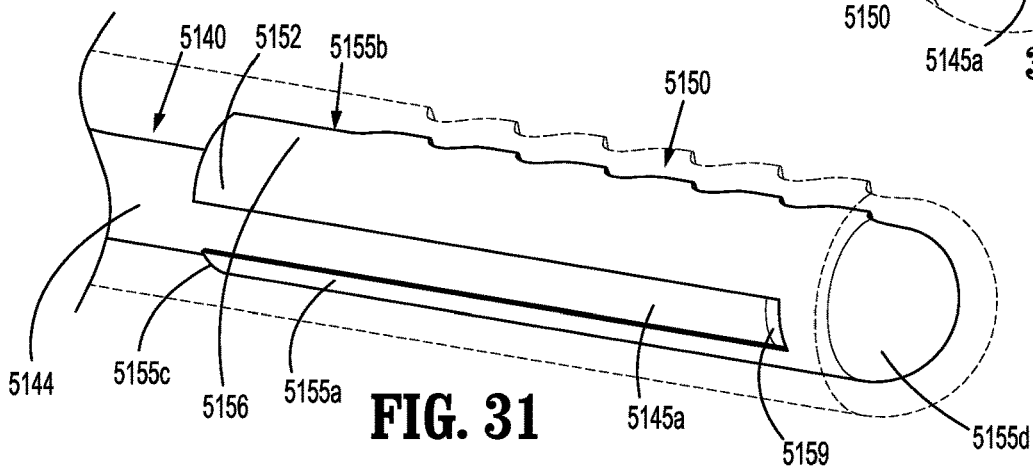
FIG. 31 is an enlarged, bottom, perspective view of the configuration of the distal end portion of the end effector assembly as illustrated in FIG. 30.
Figure 32:
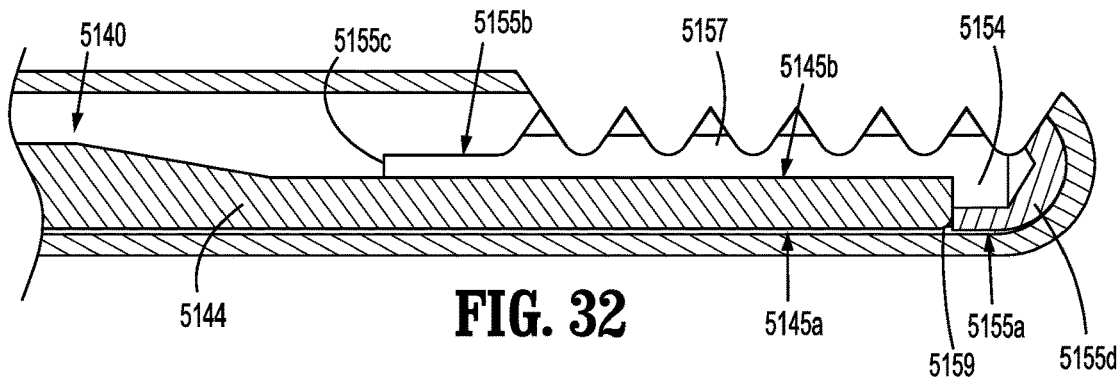
FIG. 32 is a longitudinal, cross-sectional view taken across section line "32-32" of FIG. 30.

Referring to FIGS. 30-32, another configuration of distal end portion 5144 of drive wire 5140, distal cutting tip 5150, and the engagement therebetween is shown. Except as specifically distinguished below, distal end portion 5144 of drive wire 5140, distal cutting tip 5150, and the engagement therebetween may be similar to any of the aspects detailed hereinabove.

Distal cutting tip 5150 includes a semi-cylindrical body 5152 defining a semi-cylindrical lumen 5154. Semi-cylindrical body 5152 defines a semi-cylindrical bottom surface 5155a, a planar upper surface 5155b defined by first and second side walls 5156 that are spaced apart from one another to define an elongated mouth 5157 providing access to semi-cylindrical lumen 5154, an open proximal end 5155c, and an at least partially closed distal end 5155d. Distal cutting tip 5150 further defines a longitudinally-extending slot 5159 through semi-cylindrical bottom surface 5155a opposite elongated mouth 5157. Slot 5159 has an open proximal end at the proximal end of distal cutting tip 5150.

Distal end portion 5144 of drive wire 5140 is at least partially received within and engaged with distal cutting tip 5150. More specifically, distal end portion 5144 of drive wire 5140 is received within semi-cylindrical lumen 5154 such that the at least a portion of semi-cylindrical bottom surface 5145a of distal end portion 5144 of drive wire 5140 extends into slot 5159 of distal cutting tip 5150. In this manner, distal end portion 5144 of drive wire 5140 is permitted to be further seated within distal cutting tip 5150 whereby, rather than planar upper surface 5145b of distal end portion 5144 of drive wire 5140 being co-planar with upper surface 5155b (defined by side walls 5156) of cutting tip 5150, planar upper surface 5145b is recessed relative to upper surface 5155b. Thus, the open volume within semi-cylindrical lumen 5154 is increased, thereby increasing the volume of tissue, fluids, and debris capable of being received therein.

Figure 33:
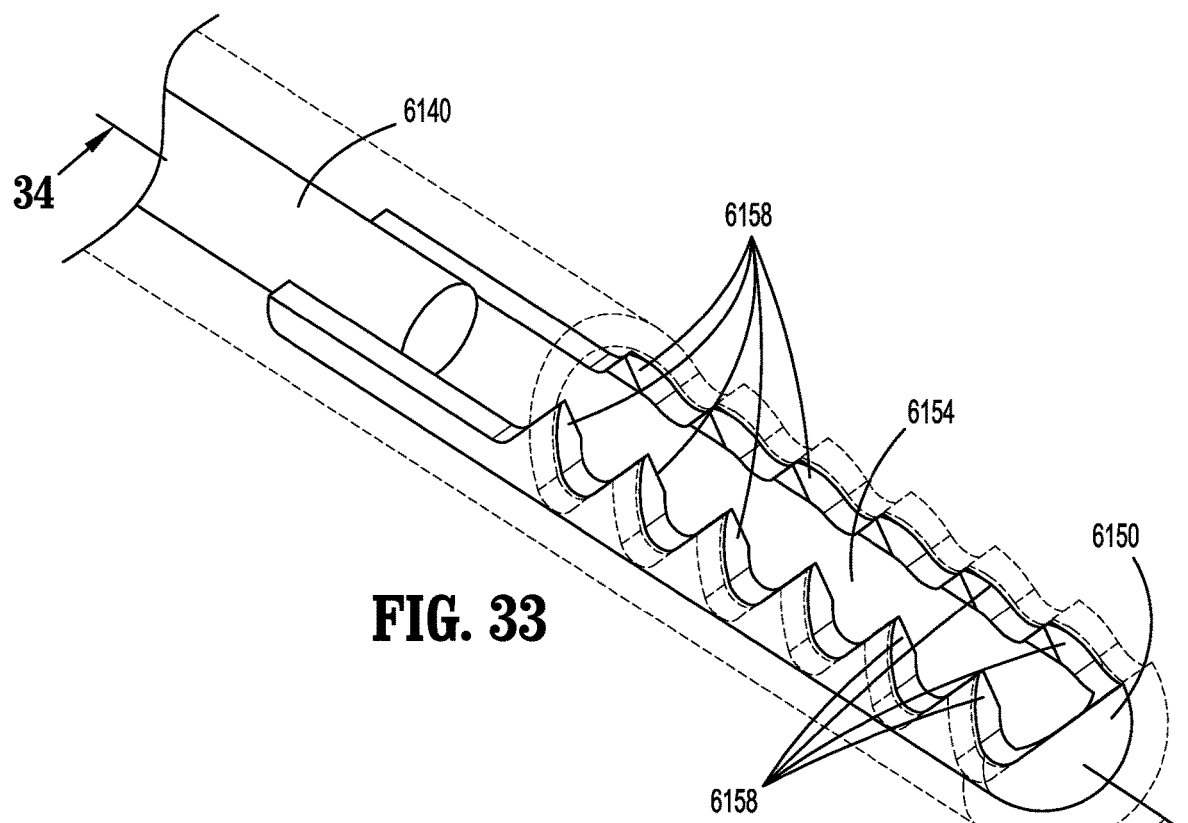
FIG. 33 is an enlarged, perspective view of another configuration of the distal end portion of the end effector assembly of FIG. 1, with the outer shaft shown in phantom.
Figure 34:
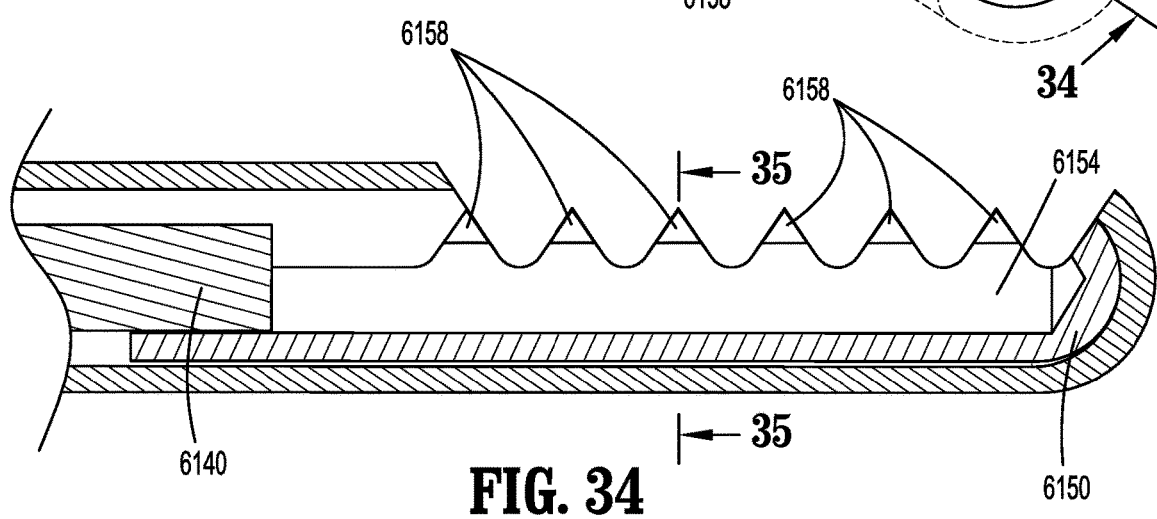
FIG. 34 is a longitudinal, cross-sectional view taken across section line "34-34" of FIG. 33.
Figure 35:
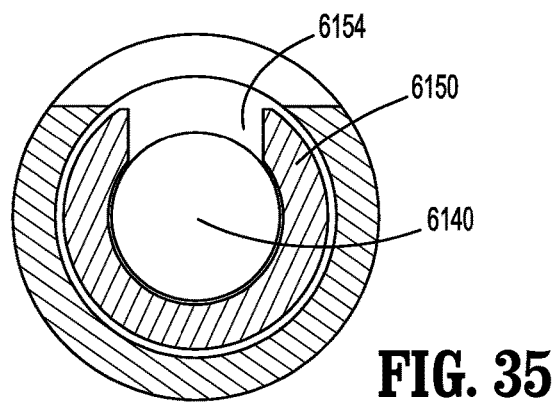
FIG. 35 is a transverse, cross-sectional view taken across section line "35-35" of FIG. 34.

Turning to FIGS. 33-35, another configuration of drive wire 6140, distal cutting tip 6150, and the engagement therebetween is shown. Except as specifically distinguished below, drive wire 6140, distal cutting tip 6150, and the engagement therebetween may be similar to any of the aspects detailed hereinabove.

Drive wire 6140 does not include a material-removed distal end portion but, rather, defines a cylindrical configuration to the distal end thereof. An outer diameter of drive wire 6140 generally approximates (e.g., is within 10%) of an inner diameter of semi-cylindrical lumen 6154 of distal cutting tip 6150. The distal end of drive wire 6140 extends to or minimally into semi-cylindrical lumen 6154 of distal cutting tip 6150 and is engaged with distal cutting tip 6150, e.g., via welding (lap welding or butt welding, for example) at a position proximally-spaced from cutting teeth 6158 of distal cutting tip 6150. More specifically, in embodiments, the distal end of drive wire 6140 extends into semi-cylindrical lumen 6154 of distal cutting tip 6150 a distance of no more than 20% of a length of distal cutting tip 6150, in other embodiments, a distance of no more than 17% of the length of distal cutting tip 6150 and, in still other embodiments, a distance of no more than 15% of the length of distal cutting tip 6150. Thus, the open volume within semi-cylindrical lumen 6154 of distal cutting tip 6150 is maximized.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as examples of particular embodiments. Those skilled in the art will envision other modifications within the scope and spirit of the claims appended hereto.

Although the foregoing disclosure has been described in some detail by way of illustration and example, for purposes of clarity or understanding, it will be obvious that certain changes and modifications may be practiced within the scope of the appended claims.

What is claimed is:

1. An end effector assembly of a tissue-resecting device, the end effector assembly comprising:
    an outer shaft defining a proximal end portion and a distal end portion, the distal end portion of the outer shaft defining a window therethrough;
    a drive wire extending through the outer shaft and including a cylindrical body and a distal end portion defining a semi-cylindrical configuration including a semi-cylindrical bottom surface and a planar upper surface, wherein a semi-cylindrical cut-out is defined within the planar upper surface; and
    a distal cutting tip disposed within the outer shaft and at least partially overlapping the window, the distal cutting tip defining a semi-cylindrical lumen defined by a semi-cylindrical bottom surface and an open top,
    wherein the distal end portion of the drive wire is at least partially received within the semi-cylindrical lumen of the distal cutting tip and engaged therein with the semi-cylindrical bottom surface of the distal end portion of the drive wire substantially mating with the semi-cylindrical bottom surface of the distal cutting tip, the drive wire configured to drive rotation or oscillation of the distal cutting tip relative to the outer shaft.

2. The end effector assembly according to claim 1, wherein the distal cutting tip includes a plurality of teeth extending along a portion of a length thereof, the plurality of teeth including a first set of teeth disposed on a first side of the semi-cylindrical lumen and a second set of teeth disposed on a second, opposite side of the semi-cylindrical lumen.

3. The end effector assembly according to claim 2, wherein a distal end of the distal end portion of the drive wire does not extend distally beyond a first tooth of each of the first and second sets of teeth.

4. The end effector assembly according to claim 2, wherein a distal end of the distal end portion of the drive wire is positioned proximally of the plurality of teeth.

5. The end effector assembly according to claim 2, wherein the drive wire is proximal to a most-proximal tooth on either side of distal cutting tip.

6. The end effector assembly according to claim 1, wherein the drive wire includes a transition portion disposed between the cylindrical body and the distal end portion, the transition portion including a curved surface.

7. The end effector assembly according to claim 6, wherein the semi-cylindrical cut-out includes a transition portion defined within the transition portion of the drive wire, the transition portion of the semi-cylindrical cut-out defined by a curved bottom surface.

8. The end effector assembly according to claim 1, wherein the distal end portion of the drive wire includes a beveled distal surface.

9. The end effector assembly according to claim 8, wherein the beveled surface of distal end portion of the drive wire is proximal of a most-proximal cutting tooth of the distal cutting tip.

10. The end effector assembly according to claim 1, wherein the semi-cylindrical cut-out defined in the drive wire is open to both the distal end portion of the drive wire and the planar upper surface.

11. The end effector assembly according to claim 10, wherein the planar upper surface is bifurcated into surface portions on either side of the semi-cylindrical cut-out.

12. The end effector assembly according to claim 11, wherein the semi-cylindrical cut-out defines a substantially constant diameter along the distal end portion.

13. An end effector assembly of a tissue-resecting device, the end effector assembly comprising:
    an outer shaft defining a proximal end portion and a distal end portion, the distal end portion of the outer shaft defining a window therethrough;
    a drive wire extending through the outer shaft, wherein the drive wire includes a semi-cylindrical cut-out; and
    a distal cutting tip disposed within the outer shaft and at least partially overlapping the window, the distal cutting tip defining a semi-cylindrical lumen defined by a semi-cylindrical bottom surface and an open top,
    wherein a distal end portion of the drive wire is at least partially received within the semi-cylindrical lumen of the distal cutting tip and engaged therein, the drive wire configured to drive rotation or oscillation of the distal cutting tip relative to the outer shaft.

14. The end effector assembly according to claim 13, wherein the drive wire includes a cylindrical body and wherein the distal end portion of the drive wire defines a semi-cylindrical configuration including a semi-cylindrical bottom surface and a planar top surface, the semi-cylindrical cut-out defined within the planar top surface.

15. The end effector assembly according to claim 14, wherein the drive wire includes a transition portion disposed between the cylindrical body and the distal end portion.

16. The end effector assembly according to claim 14, wherein the planar top surface of the distal end portion of the drive wire is recessed relative to the open top of the distal cutting tip.

17. The end effector assembly according to claim 13, wherein the distal cutting tip includes a plurality of teeth extending along a portion of a length thereof, the plurality of teeth including a first set of teeth disposed on a first side of the semi-cylindrical lumen and a second set of teeth disposed on a second, opposite side of the semi-cylindrical lumen.

* * * * *